US012379235B2

(12) United States Patent
Travers et al.

(10) Patent No.: US 12,379,235 B2
(45) Date of Patent: Aug. 5, 2025

(54) COMPACT TARGET FLOW METER

(71) Applicant: Coroflo Limited, Rush (IE)

(72) Inventors: James Travers, Rush (IE); Francesca Sorgini, Rush (IE)

(73) Assignee: Coroflo Limited, Dublin (IE)

( * ) Notice: Subject to any disclaimer, the term of this patent is extended or adjusted under 35 U.S.C. 154(b) by 0 days.

(21) Appl. No.: 18/936,244

(22) Filed: Nov. 4, 2024

(65) Prior Publication Data

US 2025/0109974 A1    Apr. 3, 2025

Related U.S. Application Data

(63) Continuation-in-part of application No. PCT/EP2023/061995, filed on May 5, 2023.

(30) Foreign Application Priority Data

May 6, 2022   (GB) ...................................... 2206658

(51) Int. Cl.
G01F 1/28       (2006.01)
A61B 5/0265     (2006.01)
A61B 5/087      (2006.01)

(52) U.S. Cl.
CPC .............. *G01F 1/28* (2013.01); *A61B 5/0265* (2013.01); *A61B 5/087* (2013.01)

(58) Field of Classification Search
CPC ................................ G01F 1/28; A61B 5/0265
(Continued)

(56) References Cited

U.S. PATENT DOCUMENTS 881,586 A     10/1908  Howe-Gould
3,857,277 A   12/1974  Moore
(Continued)

FOREIGN PATENT DOCUMENTS

CN    111504395      8/2020
DE    102010030045   12/2011
(Continued)

OTHER PUBLICATIONS

ISR/WO from corresponding PCT/EP2023/061995.

*Primary Examiner* — Nathaniel T Woodward
(74) *Attorney, Agent, or Firm* — Scherrer Patent & Trademark Law, P.C.; Stephen T. Scherrer; Monique A. Morneault

(57) ABSTRACT

A flow measurement device is provided. The flow measurement device comprising a rigid housing defining a flow channel having a channel input and a channel output, the flow channel being configured to allow a fluid medium to flow from the channel input to the channel output; a moving member hingeably mounted within the flow channel, and extending transverse to a direction of flow of the fluid medium, the moving member comprising a moving member magnet, the moving member operatively moving on exposure to a drag force resultant from fluid passing in the flow channel, where the moving member is formed from a flexible supporting structure forming a living hinge, the moving member magnet being coupled to the flexible supporting structure; a fixed magnet, provided at least proximal to a side-wall of the flow channel, the fixed magnet having like polarity with respect to moving member magnet, and being arranged to operatively exert a repulsive force on the moving member magnet thereby limiting its displacement proportionally to the magnitude of the drag force exerted by the fluid flow, so to linearise a relationship between a rate of flow of the fluid medium and moving member displacement;

(Continued)

and a sensing element located relative to the moving member and configured to provide an output indicative movement of the moving member within the flow channel.

19 Claims, 21 Drawing Sheets

(58) Field of Classification Search
USPC .................................................. 73/861.71
See application file for complete search history.

(56) References Cited

U.S. PATENT DOCUMENTS

| | | | |
|---|---|---|---|
| 6,675,660 B1 * | 1/2004 | Mosier | G01F 1/7088 |
| | | | 977/955 |
| 6,681,645 B1 | 1/2004 | Feller | |
| 8,783,088 B2 | 7/2014 | Weaver | |
| 8,800,473 B1 | 8/2014 | DeVerse et al. | |
| 2016/0252589 A1 * | 9/2016 | Raman | G01R 33/0029 |
| | | | 324/224 |

FOREIGN PATENT DOCUMENTS

| | | | | |
|---|---|---|---|---|
| EP | 1376635 | | 4/2005 | |
| FR | 3006761 | | 12/2014 | |
| GB | 2499995 | | 9/2013 | |
| JP | H07294542 | | 11/1995 | |
| JP | 2008089320 | | 4/2008 | |
| JP | 2018036218 | | 3/2018 | |
| WO | 9836245 | | 8/1998 | |
| WO | 1999050621 | | 10/1999 | |
| WO | WO-2015019128 A1 * | 2/2015 | | F16K 15/06 |

* cited by examiner

COMPACT TARGET FLOW METER

FIELD OF THE INVENTION

The present invention relates to a miniaturised flow sensing method for fluid media. It relates to a sensing technology that allows for the real-time, accurate and stable measurement of the volume of a fluid, gas or liquid, passing through a channel, and provides a wide dynamic sensing range, especially when used in channels with a cross sectional area of the dimensions of squared millimetres.

BACKGROUND

Many methods have been employed in flow sensing in restricted form-factors; primary among these are thermal methods-anemometry, calorimetry, and time-of-flight, to name a few. These methods are well suited for low-flow rates but suffer from saturation at higher rates, especially in media with high thermal conductivity such as water.

Another drawback is that sensor placement and channel geometry is critical, and sensitivity to flow orientation and regime (turbulent/laminar) is hard to avoid.

A simple alternative to the thermal approach is the target flow meter (also referred to as vane flow meter or paddle flow meter), where a physical target partially blocks the channel; the displacement or strain on this target due to the force of the flow is translated to the flow measurement. While conceptually simple, this type of meter has some limitations. The first of these arises from the fact that the force of flow increases quadratically with flow rate; this inherently limits the turndown ratio (dynamic range) as a 10× increase in flow will imply a 100× increase in force on the target.

A further complication, especially in the context of flow metering in restricted spaces, is that the target needs to be hinged in order to register deflection. A traditional mechanical hinge will have variable frictional resistance which could swamp the deflection force at low flow rates. A living hinge (sometimes called an integral hinge and being a thin flexible hinge made from the same material as the two rigid pieces it connects) can circumvent this problem but only if the hinge material is perfectly elastic; viscoelastic materials such as plastics exhibit similar frictional effects albeit internal to the material. Considering elastic materials, the most common of these are metals which are also characterised by a higher modulus of elasticity. This means that, even in very thin sheets, their stiffness can be too high to deflect against small flow forces. This is especially the case for channel diameters of the order of millimetres.

Relevant examples of target flow meters equipped with magnets for the purpose of counteracting these limitations are mentioned in the following prior-art documents.

U.S. Pat. No. 881,586A to Howe-Gould Robert is an early example of a target flow meter. It discloses a fluid velocity meter where the fluid flow moves a vane inside a flow channel, said vane being connected to a spindle crosswise of the flow channel. The moving spindle is connected to a first magnet and is combined with a second spindle moving in an external chamber and connected to a second magnet of opposite polarity, the second spindle ending in a pointer to which the movements of the vane are transmitted through the magnets, and providing a reading of the fluid velocity on a graduated scale.

GB2499995B to Grant Needham discloses a flow meter comprising a target in a fluid flow conduit and a beam attached to said target. The beam is coupled with a sensor that moves together with the beam at the passage of the fluid in the channel. The displacement of this moveable sensor generates a signal which is detected by a static sensor and is representative of the fluid flow rate. The moveable sensor may comprise an inductive sensor, wherein each fixed sensor plate comprises a printed circuit board having at least one primary coil and at least one secondary coil.

U.S. Pat. No. 8,783,088B2 to Drew S. Weaver discloses a method and apparatus for proving a flowmeter, where a displacer moving inside a flow tube carries a magnetic target which movement is detected by inductive transducers along the flow tube, and where the signal generated by the transducers is indicative of the displacer velocity, and from which the fluid velocity can be extrapolated.

U.S. Pat. No. 8,800,473B1 to Richard DeVerse discloses a mass flowmeter constituted by a flap structure placed tranversally to the fluid flow in the channel, which allows the fluid to flow in only one direction. The flap is mounted to rotate about a shaft whose axis is perpendicular to the flow direction and is counterbalanced by a spring. A stiffer spring would restrict flow ranges to higher flow velocities, while a weaker one would result in lower flow range sensitivity. While this invention addresses the issue of counterbalancing the force that the fluid exerts onto the hinged element in the channel, it only allows for the selection of a high or low flow rate range due to the limitations of the mechanical properties of the spring. Furthermore, the nature of the mechanical components in this sensing unit makes its use tricky where the size of the channel cross-section is scaled down to millimetres.

EP1376635A1 to Paul K. Edwards discloses a switch operated by a fluid flow and formed from an assembly having a paddle at a first end, an activation magnet on a second end, and a pivot shaft between the first and the second end. A biasing magnet is positioned on the external enclosure of the sensor unit to repel the magnet on the paddle assembly, with the purpose of holding it in a non-activated, stable position in conditions of zero flow. An activation sensor interacts with the magnet on the paddle to signal the presence of flow. Although this invention relates to a paddle equipped with magnets, they are arranged outside the flow channel and mainly serve to hold the paddle in a stable, vertical position in the absence of flow.

WO1999050621A1 to Stanley E. Hawkins discloses an in-line flow meter for drip irrigation systems providing a visual flow indication of both high and low flow rates above and below a field adjustable normal flow rate. Said flow meter is constituted by a paddle in the flow channel, to which a permanent magnet is attached. The paddle hangs downward into the flow and rotates upward and downward depending on whether the flow increases or decreases. An indicator lever on the outside of the flow channel carries a second magnet that interacts with the magnet on the paddle, and its rotation mimics the angular orientation of the paddle in the flow channel through the interaction of the two magnets of opposite magnetisation. While this invention describes flow metering through a paddle and magnetic force interactions, it is meant to indicate the flow rate relative to a field-adjusted null position, corresponding to a predetermined value of flow.

U.S. Pat. No. 6,681,645B1 to Murray F. Feller discloses an apparatus for measuring the flow rate where a target in the flow channel moves by an amount that depends on the flow rate and on an external force applied to the target by means of an electromechanical transducer, which also senses the amount the target moves and converts it in a flow rate reading. Said target can be either a shaft to which a rigid vane is attached, where the shaft is rotated by an electric motor (the transducer), or a vane attached to a post, where the transducer comprises at least one electric winding connected to the post and cooperating with a permanent magnet attached to the vane.

CN111504395 discloses a rotary plate type flow measurement device with magnetic linearisation. The flowmeter comprises a rigid housing; moving member comprising a rotary plate with a moving member magnet I0; a fixed magnet and a sensing member. At low flow rates the magnets provide a low repulsive force and the repulsive force is increased as flow rate increases and the magnets become closer together, providing linearisation.

JP2008089320 describes a further rotary plate type flow measurement device, similar to that in CN111504395 which comprises a magnet attached to the moving member and a fixed magnet. The repulsion force increases as the proximity of the magnets increases. The repulsion force results in strain which is measured by strain gauge, to provide flow measurement.

Despite these known approaches that fall within the broad category of "target flow meter" based on a magnetic or inductive sensing technology, there continues to be a need for a system and methodology that will allow for the measurement of fluid volumes over a wide dynamic range and the linearisation of the sensor response, especially for miniaturised applications.

SUMMARY OF THE INVENTION

These and other problems are addressed by flow measurement device in accordance with the present teaching which comprises an arrangement of magnets, one in a hinged target and one downstream from it in the channel, the magnets being arranged relative to one another such that their respective like poles are facing one another so as to produce a repulsive force between the opposing magnets. The force vs. distance relationship of magnets is complex but the function can be approximately represented by a polynomial function of $n^{th}$ order, with order depending on the geometry of the magnets and their separation distance. Relative geometry and range of displacement can be carefully selected to make the $2^{nd}$ order component dominant, thereby counteracting the quadratic flow-force in the opposite direction and effectively linearising the force to displacement relationship of the target over a wider range with respect to other flow sensing technologies, thereby increasing the turndown ratio, or the width of the operational range of the device. This arrangement provides a reliable measurement with a wide dynamic range and a fast response especially in, but not limited to, channels of millimetric dimensions.

The preferred arrangement of the flow measurement device, or flow sensor, herein described comprises: a rigid housing defining a flow channel and dimensioned to allow a fluid media to flow from a channel input to a channel output; a hinged target member mounted in the flow channel and orientated transverse to the direction of the fluid flow, said target member comprising a permanent magnet, and on which the fluid flow will exert a drag force; a fixed element, formed from a permanent magnet embedded in the flow channel wall opposite to the target member and of like polarity, the fixed element being configured to exert a counteracting magnetic force on the target member so as to limit its displacement proportionally to the flow rate; a sensing element located externally to the flow channel, the sensing element being proximal, and orientated perpendicular, to the target member, said sensing element being configured to measure a variation of a static magnetic field generated by the target displacement, and proportional to the mass/volume flow of the fluid in the channel.

In another arrangement, the fixed permanent magnet of the flow sensor is positioned, by use of an adhesive or other fixing or clamping means, in the middle of the flow channel transverse to the flow direction and parallel to the resting position of the hinged target.

In another arrangement, the sensing element operates according to the capacitive principle and is formed from a pair of capacitive plates, with one plate on the moving target, transverse to the fluid direction, and the other plate fixed and close either to the channel input or the channel output, and transverse to the fluid direction. In this arrangement, the displacement of the hinged target caused by the fluid flow in the channel will cause a variation of the electric field between the electrode pairs, with the fluid medium as the dielectric. The sensed capacitance variation can be then converted into a flow reading by the connected electronics.

In another arrangement, the displacement of the hinged target is measured via an optical sensing method. One or more optical light-emitting transducers can be located in the proximity of the channel walls, and the displacement of the hinged target can be detected via optical time-of-flight, Doppler shift or interferometric methods applied on the light reflected from the target and detected by a receiving member on the optical transducer. The detected signal can be converted into a flow reading by the connected electronics.

In another arrangement, the hinged target is an electromagnet, which can be for example, but not only, formed from a conductive path on a flexible substrate. In this arrangement, a current is driven into the conductor so that, when the target is deflected by the fluid flow, it is subjected to the repulsive magnetic force from the magnet on the opposite side of the channel, and proportionally to the drag force. The parameters of the current driven into the conductor can be tuned according to the desired range of flow rates to be measured in the selected application.

In another arrangement, the fixed magnet at the channel output can be replaced by an electromagnet, and the sensor unit can be formed from a combination of permanent magnets and electromagnets depending on the selected application.

In another arrangement, the displacement of the hinged target, when both the magnets in the flow channel are electromagnets, is measured via an inductive sensing method. A current is driven into both the electromagnets so that, when the target is deflected by the fluid flow, it is subjected to the repulsive magnetic force from the fixed electromagnet, proportionally to the drag force. At the same time, the mutual inductance on the electromagnets will vary proportionally to the distance between the moving electromagnet and the fixed electromagnet, with the inductance variation being measured on the fixed electromagnet and converted into a flow reading by the connected electronics. The measurement electromagnet of this arrangement can also be placed at the channel input, and the inductance variation being measured between said electromagnet and the electromagnet on the moving element, with a third electromagnet or permanent magnet providing the repulsive magnetic force.

In another low-friction arrangement, instead of being connected to a living hinge, the moving target member in the flow channel is mounted transverse to the fluid flow and is connected to a pin so that the permanent magnet on the moving member moves parallel to the flow direction and towards a fixed magnet placed downstream, in the middle of the flow channel and parallel to the moving member. A sensing means located in the proximity of the flow channel detects the displacement of the moving member and its output is sent to a processing unit and translated into a flow reading.

In another arrangement, the moving target member in the flow channel is mounted transverse to the fluid flow and is supported by a plurality of living hinges such that the motion of said member remains perpendicular to the flow. In this arrangement, the moving member is pushed by the fluid medium towards a fixed magnet placed downstream in the flow channel, and transverse to the fluid flow. A sensing means located in the proximity of the flow channel detects the displacement of the moving member and its output is sent to a processing unit and translated into a flow reading.

In order to further understand the principles that relate to the present teaching, it is convenient to describe the nature of the forces at play in the flow channel: 1) the magnetic force between two cylindrical magnets when the distance between said magnets is varied; 2) the drag force of a fluid with non-zero velocity acting on a target transverse to the fluid flow.

1) The force between two cylindrical magnets with their magnetic dipole aligned on the z-axis is proportional to the following quantity:

$$F_z \propto \frac{\pi \mu_0 M^2 r^4}{4} \left[ \frac{1}{z^2} + \frac{1}{(z+2L)^2} - \frac{2}{(z+L)^2} \right]$$

where M is the magnetization of the magnets, L is their length, r is their radius and z is the distance between them. For small values of z, this approximation becomes invalid as the force becomes large for close-to-zero distance. When L<<z, the point dipole approximation can be considered and the force along the z-direction drops proportional to $1/z^4$ for large distance z, according to the equation below:

$$F_z = \frac{3\mu_0 m_1 m_2}{2\pi z^4}$$

Where $\mu_0$ is the permeability of free space, $m_1$, $m_2$ the two dipole moments, and z is the distance between the two dipoles. However, the dipole approximation is less accurate when the separation distance z is comparable to the size of the cylindrical shaped magnets. Therefore, the relationship between magnetic force and separation distance cannot be precisely modelled and needs to be measured experimentally on a case-by-case basis.

2) The drag force exerted by a fluid onto a target perpendicular to the direction of the flow is directly proportional to the power of the fluid velocity according to the following equation:

$$F_{drag} = \frac{c_d \rho v^2 A}{2}$$

where $c_d$ is the drag coefficient, p is the fluid density, v is the fluid velocity and A is the area of the target. It is clear how the drag force on the target increases quadratically as the flow rate increases.

It will be appreciated that this makes it difficult to tune the dimensions and to select the appropriate materials for the hinged target in contact with the fluid, especially in those applications where the dynamic range of flow rates span across different orders of magnitude. In fact, low flows would cause tiny deflections, while high flows would bend the flexible member of the target irreversibly.

This interaction between the above-mentioned forces is usefully employed within the sensing technology described in the present application: the increase of the repulsive magnetic force when the magnet on the target approaches the fixed magnet on the opposite side of the channel is conveniently used to counteract the effect of the drag force that the fluid flow exerts on the target.

The linearisation effect and the range of measurable flow rates can be matched to the drag force-target displacement relationship by appropriately selecting the characteristics of the magnets and their separation distance in the flow channel, together with the geometry of the flow channel, which is another advantage of the sensing method deployed in accordance with the present teaching.

A further innovation is that of a discriminating feature between different types of media passing through the sensor. In certain liquid measurement applications, it may be desirable to detect ingress of gas which may show a small phantom reading by opening the paddle, especially in the pressure differential mode to be described later. There are many gas/bubble detection methods described in the literature such as optical, capacitive, thermal, etc. but most are too bulky to implement within the device of the present teaching. Given that many target liquids are conductive; e.g. physiological fluids (blood, milk, urine), or drinking water, a conductivity sensor is an obvious choice with a small physical footprint.

Two conductive pins attached to stimulus/sensing electronics form the conductivity sensing implementation. A complication of this approach is that, even when bulk gas is present in the channel, the features of the inside channel may remain wetted thus retaining a potential conductive pathway. It is important to be able to distinguish this condition from that of bulk liquid.

Two technological solutions are herein applied to achieve this: (a) rather than use a DC signal, which only determines resistance, AC stimulus is used to measure impedance comprising both resistive and reactive components. The reactive component can differentiate between a skin of liquid on the surface and bulk liquid in the channel; (b) as skinning is considered undesirable, the tip of each electrode is sufficiently pointed to break surface tension of liquid at the tip and provide some electrode area free from wetting.

It is worth noting that AC stimulus is generally used in liquid conductivity sensing as it avoids other pitfalls of DC stimulus such as electrode polarisation, so in this case it is an approach with additional benefit.

These and other advantages of this invention will be further understood upon consideration of the following detailed description of the embodiments and drawings.

BRIEF DESCRIPTION OF THE DRAWINGS

The accompanying drawings provide a further understanding of the sensing arrangement described in the present invention, however, they are not intended to limit the scope of the appended claims.

DETAILED DESCRIPTION

Figure 1A:
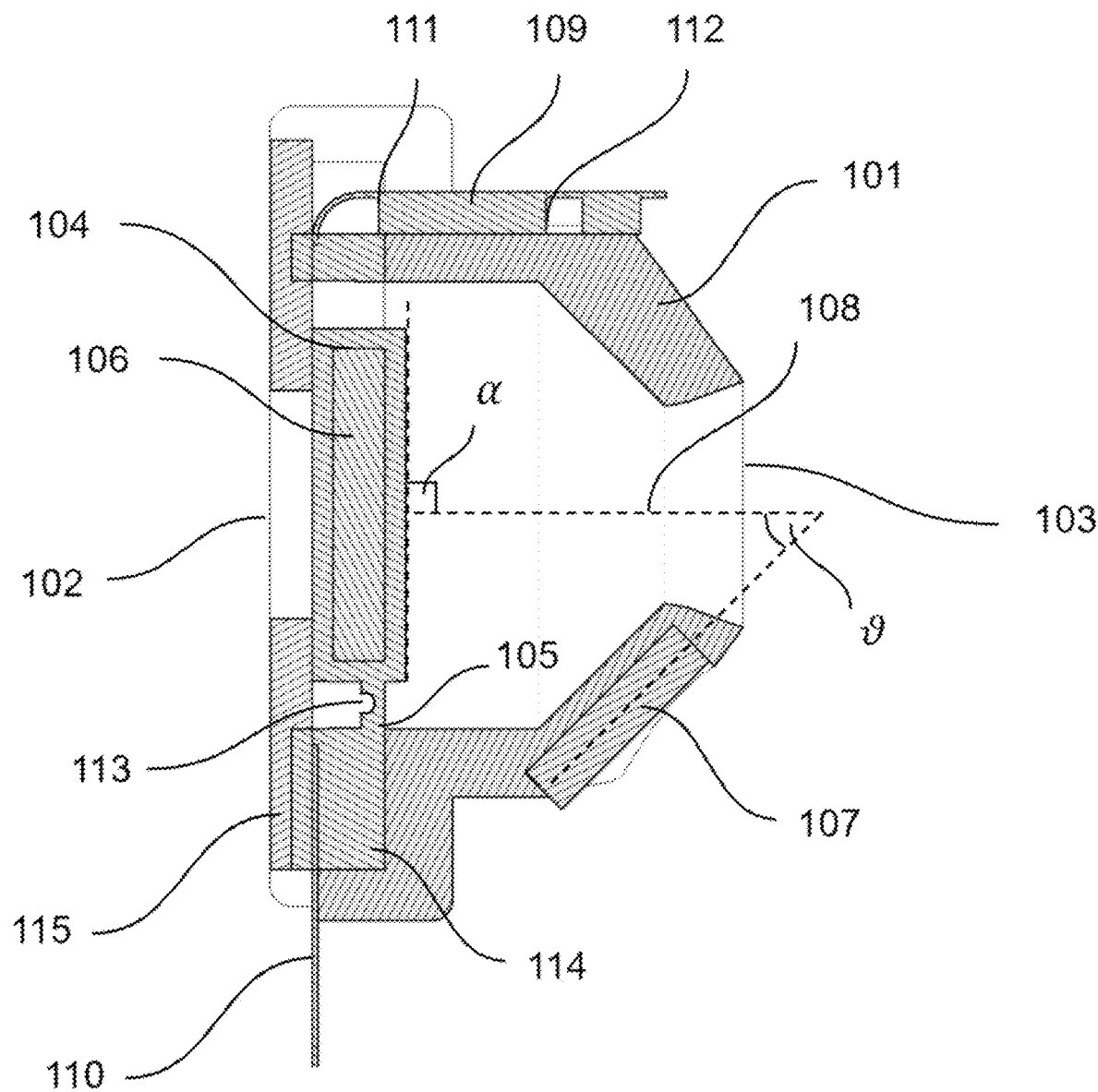
FIG. 1A is a schematic representation of the lateral section of a device in accordance with the present teaching, in a configuration of conditions of zero flow and where the sensing element is a Hall-effect sensor.
Figure 1B:
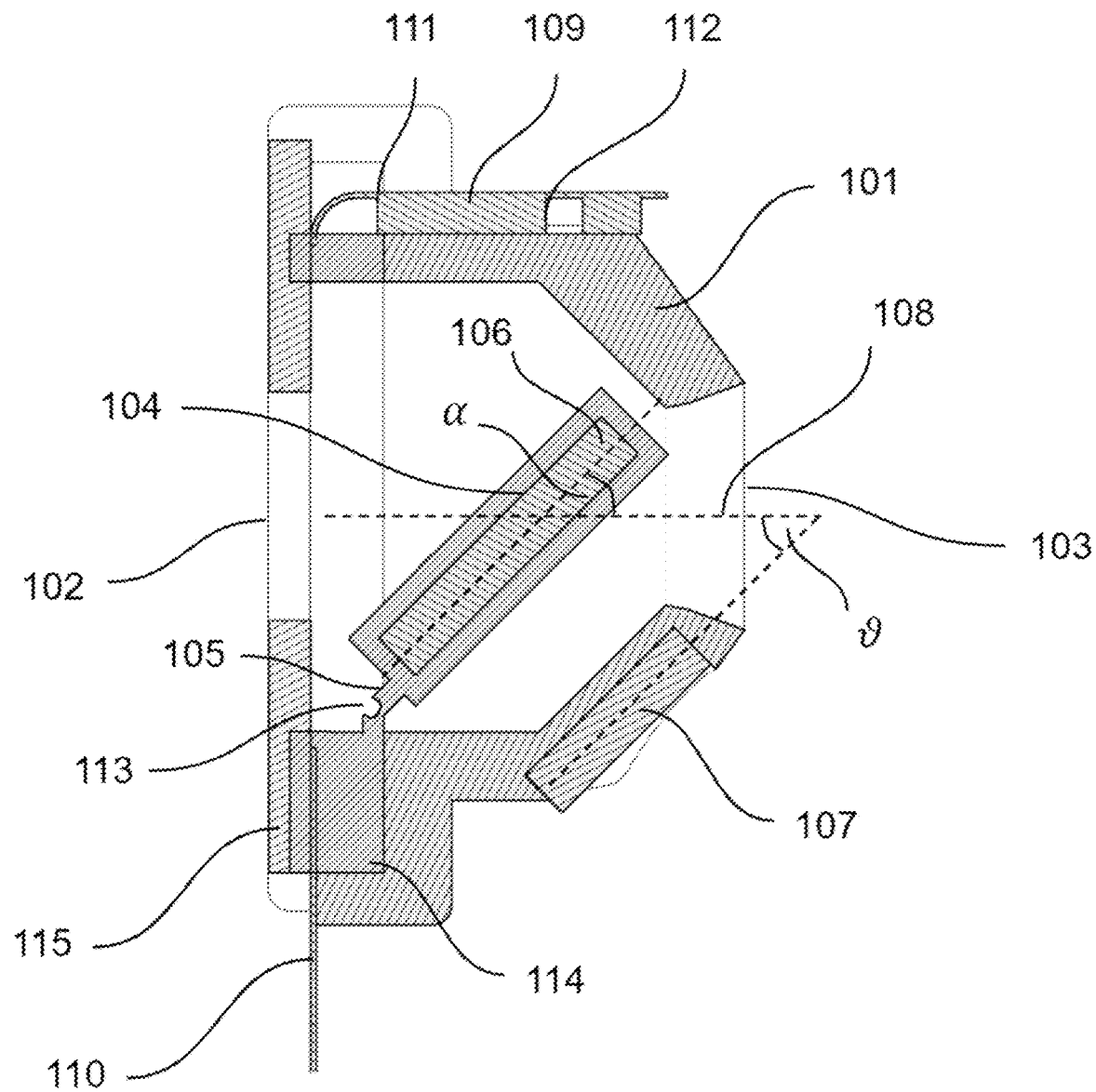
FIG. 1B is a schematic representation of the lateral section of the device of FIG. 1A, in an exemplary condition of maximum opening, corresponding to a maximum detectable flow rate, and where the sensing element is a Hall-effect sensor.
Figure 1C:
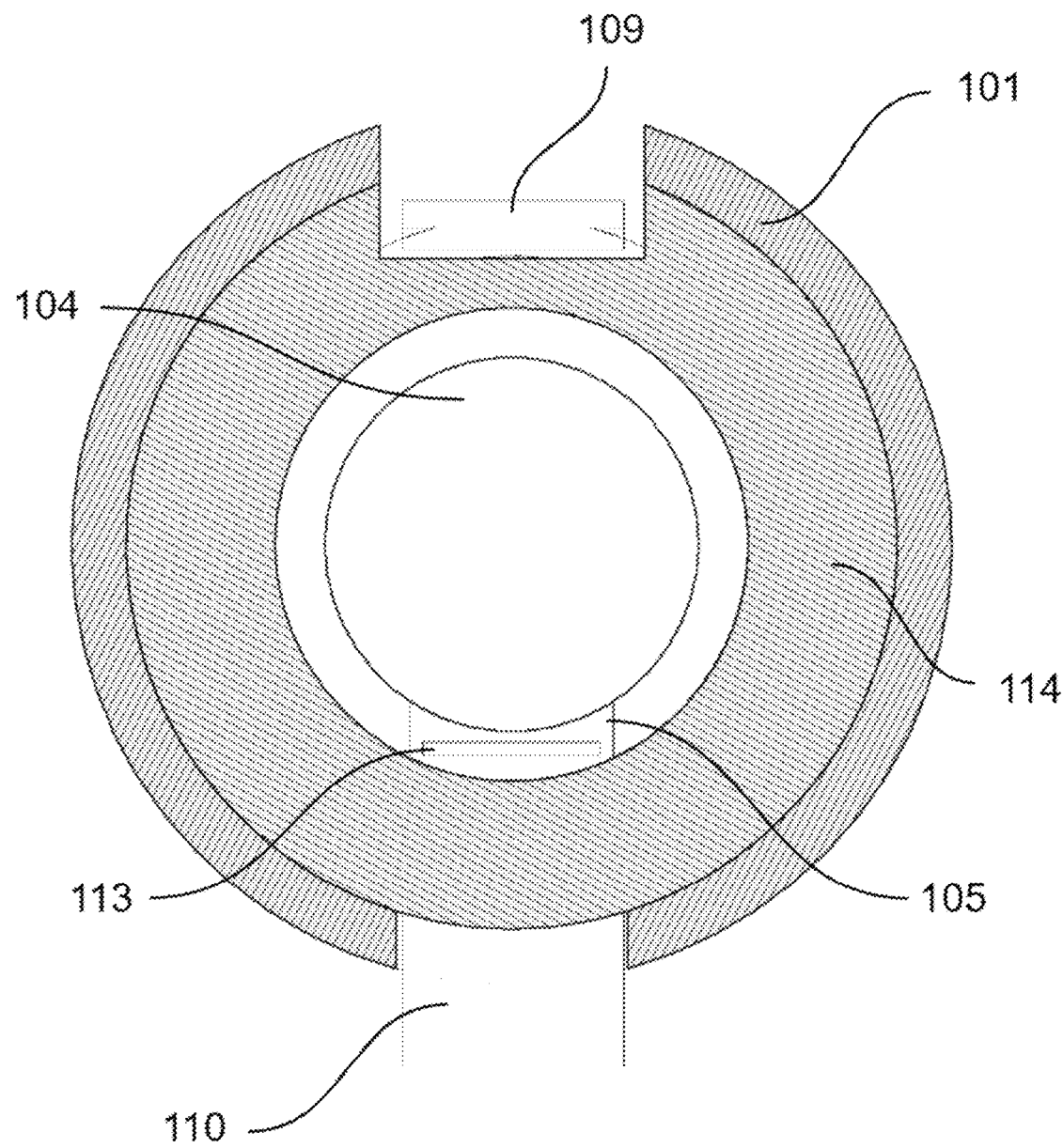
FIG. 1C is a schematic representation of the back section of the device of FIG. 1A, showing the geometry of the flow channel section and of the moving member.

Referring to FIG. 1A and FIG. 1B, there is provided a schematic representation, in section view, of a preferred arrangement of a flow sensor provided in accordance with the present teaching. Referring to FIG. 1C, there is provided a schematic representation of the back section of this flow sensor.

The sensor comprises a rigid housing (101) which defines a flow channel therein, the flow channel has an input port (102) and an output port (103). In operation a fluid will flow from the input port to the output port in a directional flow. A moving member (104) is mounted in the flow channel transverse to the direction of the fluid flow and proximal to the channel input port (102). The moving member (104) functions as a target and can hingeably move under the influence of the fluid flowing within the flow channel. The moving member has a first stationary position—as shown in FIG. 1A, and a second non-stationary position—as shown in FIG. 1B, where it has moved towards the output port (103) under the influence of the fluid moving within the fluid channel. This movement is facilitated by use of a living hinge comprising a flexible structure (105) and a permanent moving member magnet (106), and on which the fluid flow will exert a drag force. A fixed member (107) formed from a permanent magnet of like polarity with respect to the moving member magnet (106) on the moving member (104) is provided on, or embedded in, the flow channel wall, opposite to the moving member and proximal to the channel output port (103). The fixed member (107) is orientated relative to the moving member magnet and is provided so as to exert a counteracting magnetic force on the moving member magnet. Given that the moving member magnet is located on the moveable target member, this counteracting force serves to limit the displacement of the target member proportionally to the magnitude of the drag force exerted by the fluid flow.

The fixed member (107) can be embedded or otherwise located in, or on, the channel wall by means of gluing or other clamping means, with its dipole axis at an angle 'θ' with respect to the channel central axis (108). A sensing means or sensing element (109) is located on the outside of the flow channel, and in this configuration perpendicular to the moving member (104). The sensing means is sufficiently proximal to the moving member so as to be able to measure the displacement of the moving member. The sensing means is configured to provide an output indicative of the sensed displacement. These output signals can be sent to a processing unit via a flex cable (110) and are translated into a flow measurement.

In a preferred arrangement, the sensing means comprises a Hall-effect sensor. It will be appreciated that a Hall-effect sensor monitors magnetic fields with high accuracy, consistency and reliability, and it is also a cost-effective way to monitor object displacement. A Hall-effect sensor comprises a Hall element, usually formed from a thin strip of metal, onto which a current is applied. If a static magnetic field is applied perpendicularly to the direction of the current, the charge carriers experience a deflection under the Lorentz force. This effect causes a difference in electric potential (the Hall voltage) between the two sides of the strip, which is proportional to the strength of the applied magnetic field. The capability of a Hall-effect sensor to respond to static magnetic fields is the key distinction from inductive sensors, which are only sensitive to varying magnetic fields. The output voltage from the Hall element is usually tiny (microvolt range), so it is important to provide it with adequate processing circuitry such as amplification and noise suppression. Hall elements are commonly integrated into Hall sensor chips comprising signal processing and digitising circuitry thus simplifying the interfacing task.

Hall-effect sensors are widely found in industrial and consumer applications and are mainly used for proximity sensing, positioning, speed detection, and current sensing. They can be used as switches, characterised by a binary response, when combined with threshold detection, or they can be used as linear sensors when the output voltage varies proportionally to the magnetic field they are sensing.

FIG. 1A depicts the flow channel in conditions of zero flow, where the hinged target member (104) is represented in its resting position at an angle 'α'=90° with respect to the channel central axis. In order to maximise the Hall-effect sensor resolution, it is important that the sensing element (109) is correctly positioned with respect to the magnet (106) on the hinged target (104) generating the magnetic field object of the measurement: the minimum-to-maximum distance values of the sensing element must lay within the region where the greatest change in the magnetic field occurs.

In order to address this point, in the preferred arrangement the sensing element is configured such that its edge on the channel input side (111) corresponds to the edge of the permanent magnet (106) on the target when "α'=90°.

Figure 2A:
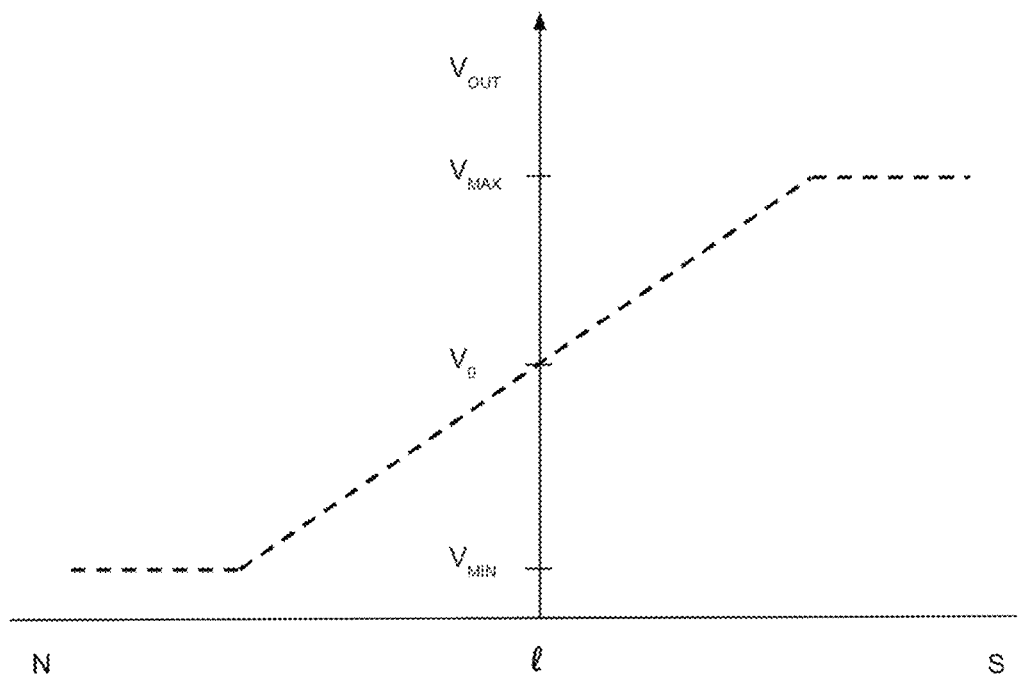
FIG. 2A is a simplified representation of the voltage response for a Hall-effect linear sensor when a magnetic field is applied along the sensor length.
Figure 2B:
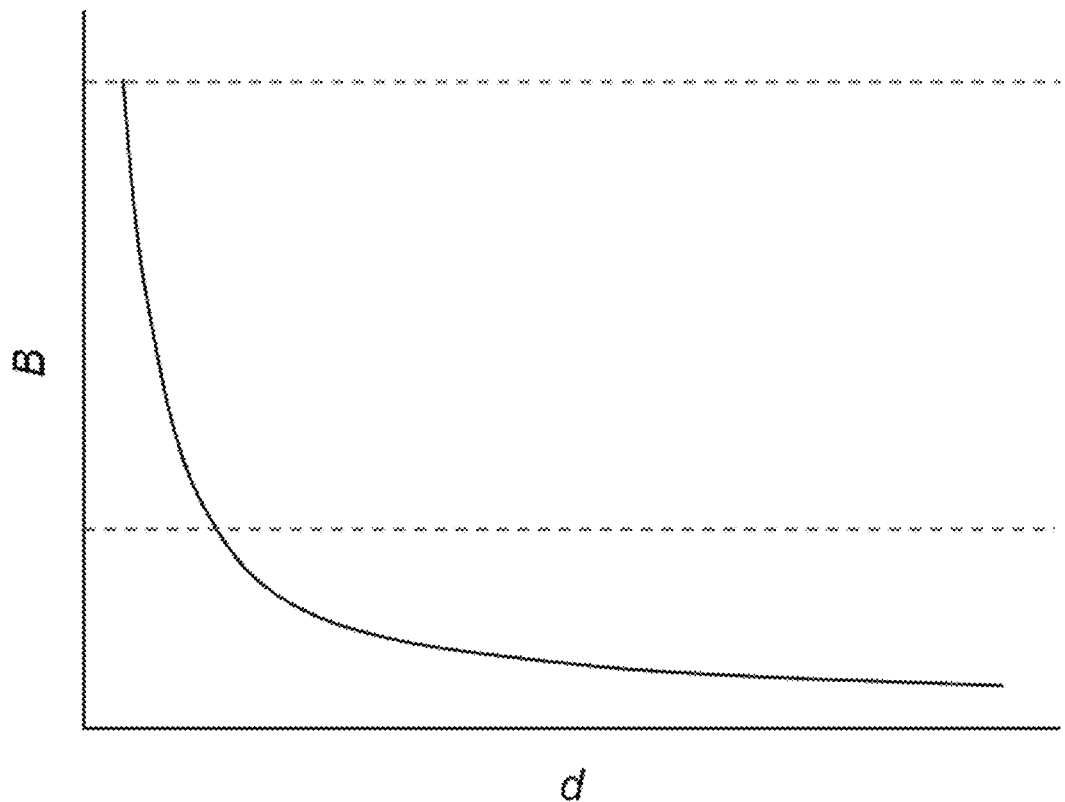
FIG. 2B is a representation of how the intensity of a magnetic field generated by a permanent magnet decays over distance from said magnet.

To further understand this concept, in FIG. 2A there is provided a simplified description of the typical voltage response of a Hall-effect linear sensor to an applied magnetic field along the sensor length l, and in FIG. 2B how the magnetic field (B) generated by a permanent magnet decays over distance (d) from said magnet.

In absence of a magnetic field, the sensor output will be equal to half the power supply voltage ($V_O$). As the applied magnetic field increases, the output voltage will either pull towards the power supply voltage value ($V_{MAX}$), corresponding to the magnetic south (S), or towards the ground ($V_{MIN}$), corresponding to the magnetic north (N). If the saturation point is reached, ideally the voltage output will not change anymore if stronger fields are applied. In reality, near saturation the sensor response presents an inflection point which indicates the end of the linear region, and the response can no longer be distinguished from the one in the sensor active region.

In order to maximise sensing resolution, it is important that the minimum-to-maximum distance values of the Hall-effect sensing element are positioned within the linear region marked with dashed horizontal lines in FIG. 2B, where the greatest change in the magnetic field occurs.

In the preferred arrangement, for the purpose of enhancing low-flow discrimination, it is convenient that the flexible member (105) of the target is clamped close to the channel input (102) so that, in the zero-flow state, the magnet on the target (106) is repelled by the fixed magnet (107) downstream and completely seals against the channel input (102). This means that, instead of the drag force being the dominant contributor to the target displacement, the pressure differential across the channel will force the target to deflect and open it even for very low flow rates. In this way, the target also constitutes a one-way valve which limits the presence of backflow affecting the measurement.

In the preferred arrangement, it is convenient that the housing of the sensing unit is manufactured with a hard material so that it is shielded from external forces and the channel geometry is preserved during the measurements. The selected material should have low magnetic permeability so as to not interfere with the magnetic field generated by the movement of the target: examples are metals such as austenitic stainless steel, or engineered plastics such as PEEK or Delrin®. Delrin will be appreciated as being an example of polyoxymethylene (POM), a high-performance acetal resin. PEEK (polyetheretherketone) is a high-performance semi-crystalline engineering thermoplastic In order to ensure the correct operation of the sensing unit and avoid any fluid leaks which could affect the sensor element, the flow channel should be completely sealed and must isolate the fluid medium inside the channel from the external environment. To achieve a complete seal around all the components of the flow channel, it is convenient that the flexible member (105) is fixed within the sensor body using appropriate adhesives or mechanical clamping means.

FIG. 1B depicts the flow channel in an exemplary condition of maximum opening, corresponding to the maximum detectable flow rate, where the hinged target (104) is at an angle "α"<90° with respect to the channel central axis.

In order to maximise the sensing range of the Hall-effect sensor, 'a' should correspond to the maximum deflection of the target for which the edge of the permanent magnet (106) on the target crosses the sensing element edge on the channel output side (112). When the target goes past said edge (112), in fact, the signal from the Hall-effect sensor is characterised by an inflection point and can no longer be distinguished from the sensor active region.

In order to maximise the linearisation of the drag force-target displacement relationship, the magnetic repulsive force should be maximised when the deflection angle of the target equals 'α'. This means that the preferred orientation for the fixed magnet (107) should be 'ϑ'='α' so that the faces of the permanent magnet (106) on the target and the fixed magnet (107) with like poles becomes parallel, with their centres ideally aligned. In the preferred arrangement 'α'='ϑ'=45°, however, the value of 'α' for which the flow rate is maximised should be calculated according to the desired measurement range and channel parameters for the selected application.

Another important aspect for the design of the sensing unit is the selection of the parameters of the permanent magnet (106) integrated in, or provided on, the moving member (104). The magnetic strength of the magnet (106) should be of a suitable value so that the Hall-effect sensor can operate in its linear range without saturating, while the magnet's (106) thickness should allow it to move within the sensing range of the Hall-effect sensor in order to obtain as fine a resolution as possible. The magnet's (106) cross-sectional area should be selected instead according to two main design constraints: the ratio between the cross-sections of the channel and the moving element (104) should maximise the drag force that the fluid exerts onto the moving element; the magnet's (106) surface area should be such that, in the position of maximum channel aperture, the faces of said magnet (106) and of the fixed magnet (107) with like poles will be aligned, and any fringing effect due to the magnetic field lines coming out from the magnets' sides will be minimised. Fringing will in fact lead the moving element (104) to deviate from its trajectory and flip away from the magnets' central axis, thus exposing to the fixed magnet (107) an opposite magnetic pole. Once the right geometry for the magnet (106) on the moving 17ocketement (104) is defined, the dynamic range of measurement can be further adjusted by selecting the right thickness for the fixed magnet (107), the strength for both of the magnetic elements (106, 107) and their separation in the channel. Another advantage of the present teaching is that, keeping all the geometric parameters unvaried, the dynamic range can be also adjusted by either replacing the magnetic elements with others of a different magnetic strength, suitable for the Hall-effect sensor to keep working within its linear range, or by using a plurality of magnetic elements, adding or removing the magnets until the desired magnetic repulsive force is obtained.

In another exemplary arrangement, the sensing member is a magnetoresistive element, where the change of electrical resistance of the sensor is proportional to the magnetic field applied on it. The sensing member can be based on one of the magnetoresistive effects which are typical of different materials, such as: geometrical magnetoresistance, positive magnetoresistance, and Shubnikov-de Haas oscillations, i.e. oscillations in the conductivity of a material in the presence of very intense magnetic fields, typically found in bulk non-magnetic metals and semiconductors; negative magnetoresistance or anisotropic magnetoresistance, AMR, typically found in magnetic metals; giant magnetoresistance, GMR, tunnel magnetoresistance, TMR, colossal magnetoresistance, CMR, and extraordinary magnetoresistance, EMR, typically found in multicomponent or multilayer systems.

In this arrangement, the change in the sensor resistance due to the movement of the target (104) is measured by the electronics connected to the sensing element (109) through a flex cable (110) and is sent to a processing unit where it will be translated into a flow measurement.

An example of permanent magnets which can be integrated in the sensing unit is neodymium (NdFeB) magnets. The advantage of neodymium magnets is their high strength: they have high levels of magnetism and are very resistant to demagnetisation when compared to other magnetic compounds like ferrite and even samarium-cobalt.

They also have the advantage of being relatively cheap and are manufactured in a wide range of sizes, even with diameters as small as 1 mm which allows them to be used for miniaturised applications.

In the context of flow measurement, it is advantageous that the magnetic elements in contact with the fluid medium are protected against moisture penetration which can cause corrosion with detrimental effects on the structural integrity and the performance of the magnets, especially in those applications where it is paramount to avoid any contamination of the measured fluid (medical, food industry, etc.).

In order to address this issue, the magnets can be encapsulated with inert coatings such as, but not limited to, epoxies or polymeric materials such as silicone rubber.

As shown in FIG. 1B and FIG. 1C, the hinging area (113) can advantageously include a feature of semicircular cross-section indented in the polymeric structure that provides the living hinge, and it should extend for almost the total width of the living hinge (105). The vertical positioning of the hinging area (113) should also be far enough from the channel wall, so that the living hinge (105) will allow the flexible support to bend without interfering with the channel wall structure.

Another useful configuration for the hinging area (113) is that it should ideally be located on the side of the living hinge (105) which is facing the channel input (102), so that the edges of the hinging area (113) will not come in contact with each other when the moving member (104) is displaced by the flow rate. It is understood that the ideal geometry and depth of the cross section of the hinging area (113) should be determined according to the selected application and to the material selected for the living hinge (105).

The already mentioned problem of the hinge present in the known target flow meters is also addressed by the present invention in that the living hinge is no longer required to provide repelling force to the flow, as the magnets now satisfy this requirement. In the preferred arrangement, the living hinge (105) supporting the magnet (106) on the moving member can therefore be made of polymeric, non-magnetic materials as long as the hinging area (113) is thin enough to render the internal frictional forces negligible in comparison to the magnetic repulsion. A polymeric material such as, but not limited to, silicone rubber of adequate shore hardness can offer several advantages for the manufacturing of the living hinge:

- it would be suitable for both the fabrication of the living hinge itself, as well as the entire supporting structure for the magnetic element, guaranteeing its complete encapsulation and insulation from the fluid medium while being easily manufacturable via injection moulding;
- the living hinge (105) itself can become part of a more complex structure like a gasket (114) between the channel structure and any clamping means (115), conveniently sealing the flow channel; and
- the ideal compression amount of said gasket (114) can be achieved for each application with an adequate dimensioning of the rubber thickness and shore hardness.

Another important aspect of the present invention, which can be appreciated with reference to the cross-sections in FIG. 1B and FIG. 1C, is that the cross-section of the flow channel, defined by the rigid housing (101), and of the moving element (104) should preferably be circular in order to limit vorticity or turbulence in the flow channel, and to maximise the effect of the fluid drag force on the moving element (104). In addition to that, the ratio between the cross-sectional areas of the flow channel and of the moving element (104) should be optimised in order to achieve a pressure differential between the channel input port (102) and output port (103) suitable for the channel opening also in conditions of flow rates as low as 10 µl/s.

The capability of addressing such low flow rates and extending the dynamic range of measurement up to much higher volumes, depending on the selected geometry of the channel and the parameters of the sensor unit components, and the possibility of measuring different fluids including air, makes the flow sensor of the present invention suitable for a range of applications. Also, the sensor construction and its fast response time makes it particularly suitable for the real-time measurement of pulsatile flow, which is common in biomedical applications.

Biomedical applications where the flow sensor of the present teaching can be of particular advantage are, but are not limited to:

- blood flow monitoring, where the blood flow rate highly depends by the distance from the heart and the size of the vessel, and can range from 20 µl/s in small vessels up to 16 ml/s when the blood is pumped from the heart directly in the aorta;
- breath monitoring, for example for the measurement of the peak expiratory flow rate, which typical values span from 130 L/min in paediatric subjects to 600 L/min in adult males;
- human milk secretion, for example during breastfeeding, with typical milk flow rates ranging from 10 µl/s to at least 5 ml/s; and
- urine excretion, for which typical flow rate ranges are between 10 ml/s to 21 ml/s in adults.

Figure 3:
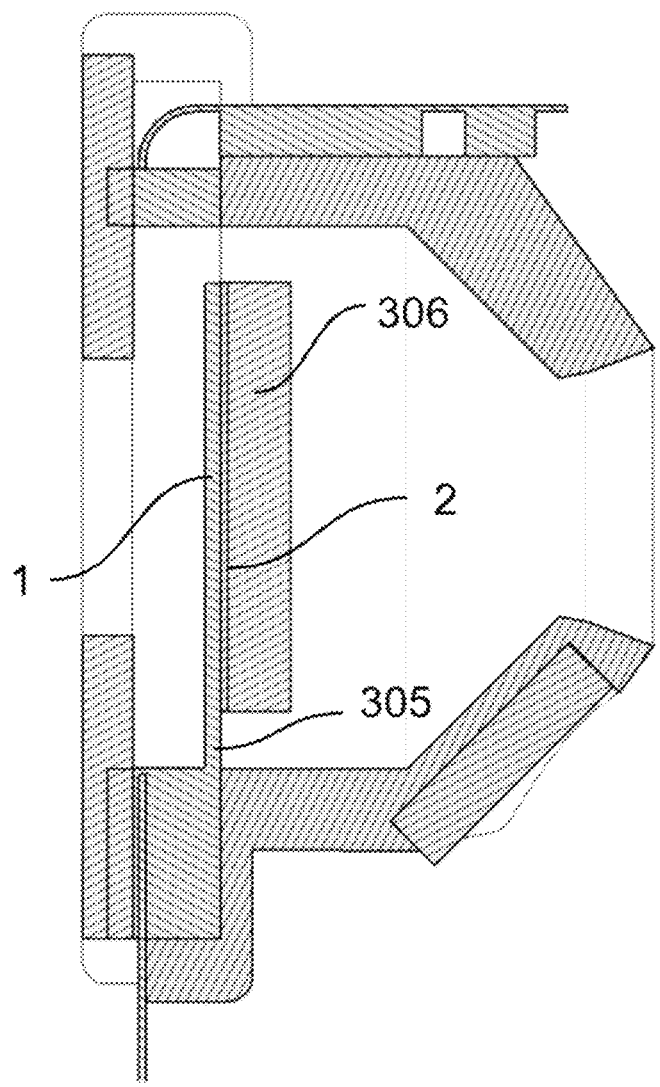
FIG. 3 is a schematic representation of the lateral section of an alternative arrangement of the device of FIG. 1A, where the moving member is formed from a flexible structure and a permanent magnet is attached to it by means of an adhesive or other clamping means.

In another arrangement, such as the one presented in FIG. 3, the magnet on the target (306) can be fixed onto a flexible supporting structure (1), also constituting the living hinge (305), by gluing or other clamping means. Said structure should be manufactured with a thin, flexible polymeric film such as, but not limited to, PEEK or Polyimide. As mentioned above, the geometry and thickness of said flexible structure will be selected in order to obtain the optimal mechanical properties for the range of flow rates to be measured and to minimise internal frictional forces against the magnetic repulsion. In addition to that, a moisture-resistant coating should be applied to the flexible film-magnet assembly to preserve the integrity of the magnetic element (306) and of the adhesive layer (2).

Figure 4:
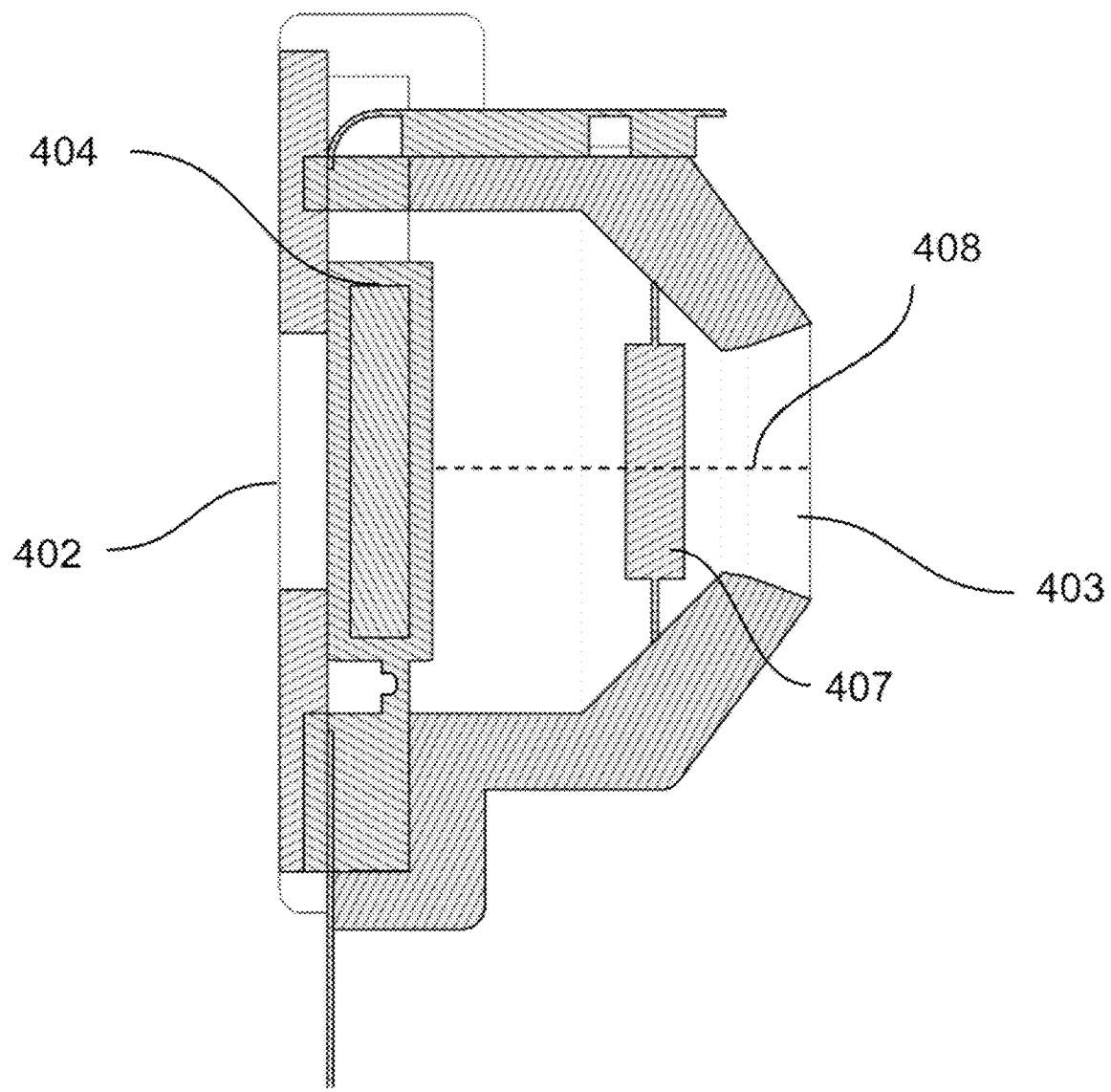
FIG. 4 is a schematic representation of the lateral section of an alternative arrangement of the device of FIG. 1A, where the fixed magnet is placed in the middle of the flow channel, transverse to the fluid flow and parallel to the resting position of the moving member.

FIG. 4 represents an alternative arrangement, in section view, of the device of FIG. 1A where the fixed magnet (407) is placed between the input port (402) and the output port (403) of the flow channel, closer to the output port (403) and transverse to the fluid flow. The fixed magnet (407) can be conveniently placed, by means of gluing or other clamping means, in a suspended position along the channel middle axis (408) and aligned with the resting position of the hinged target (404). In this arrangement, the fixed magnet (407) will restrict the cross-sectional area of the flow channel, with the fluid flow passing between the fixed magnet and the channel wall.

Figure 5A:
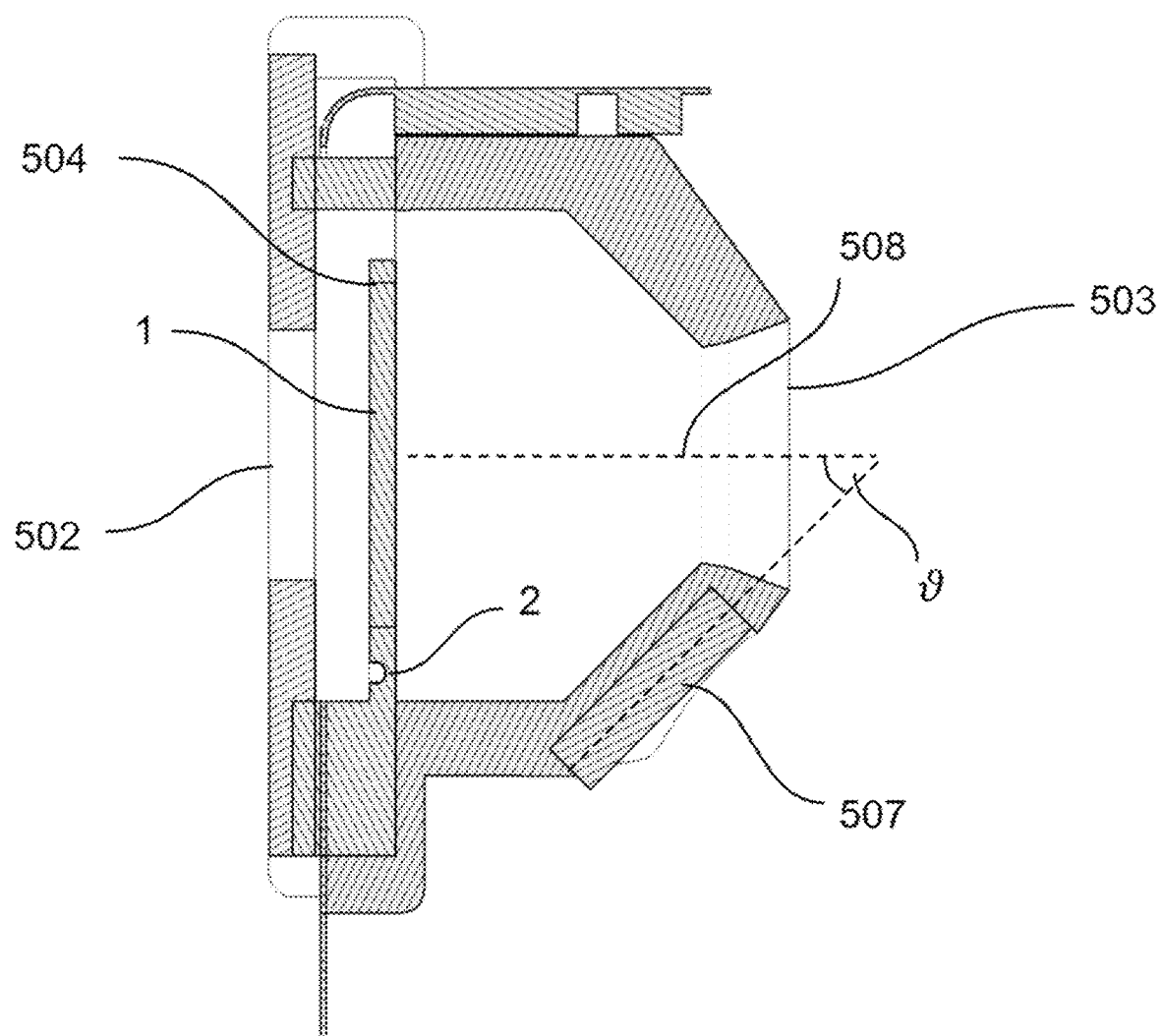
FIG. 5A is a schematic representation of the lateral section of an alternative arrangement of the device of FIG. 1A, where the moving member comprises an electromagnet.

FIG. 5A represents an alternative exemplary arrangement of the device of the present teaching, in section view, where the hinged target (504) is an electromagnet, and the fixed magnet (507) is embedded in the channel wall at an angle '$\vartheta$' with respect to the flow channel central axis (508). The electromagnet can be conveniently constituted by a conductive path (1) on a flexible substrate (2) such as a flat-flex-cable (FFC) or flexible-printed-circuit (FPC), or alternatively using traditional methods such as flat winding of magnet wire. In this arrangement, a current is driven into the conductor (1) so that, when the target is deflected by the fluid flow, it is subjected to the repulsive magnetic force from the fixed magnet (507) on the opposite side of the channel, and proportionally to the drag force.

Figure 5B:
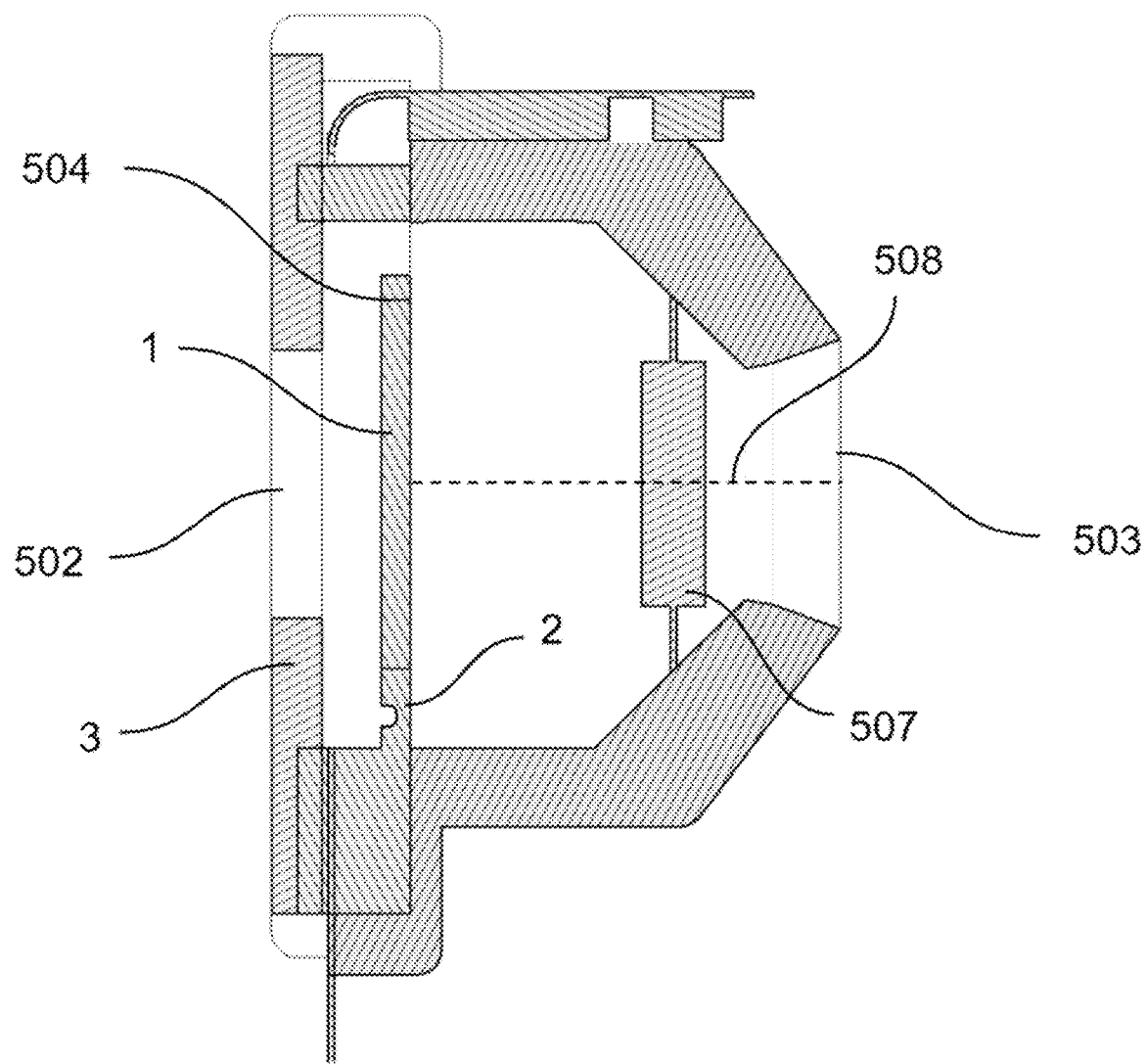
FIG. 5B, where the moving member comprises an electromagnet, and either a fixed magnet or a second electromagnet is placed in the middle of the flow channel, transverse to the fluid flow and parallel to the resting position of the moving member, and where the displacement of the moving member can be measured with an external sensing unit or by inductive sensing technology.

FIG. 5B represents an alternative exemplary arrangement of the device of FIG. 5A, in section view, where the fixed magnet (507) is placed between the input port (502) and the output port (503) of the flow channel, closer to the output port (503) and transverse to the fluid flow, in a suspended position along the channel middle axis (508) and aligned with the resting position of the hinged target (504).

In another arrangement, the sensor unit described in FIG. 5A-B can comprise an electromagnet in place of a fixed magnet at the channel output, generating an opposing magnetic force on the hinged target (504). It is understood that the sensor unit can be constituted by a combination of permanent magnets and electromagnets, depending on the selected application.

When both the magnets of the embodiment in FIG. 5B are electromagnets, the displacement of the moving member (504) can be also measured via inductive sensing technology. In this arrangement, a current is driven into both the conductor (1) on the moving member (504) and into the conductor (507) fixed downstream in the channel so that, when the target is deflected by the fluid flow, it is subjected to the repulsive magnetic force from the fixed electromagnet (507) proportionally to the drag force. At the same time, the mutual inductance on the electromagnets will vary proportionally to the distance between the moving member (504) and the fixed electromagnet (507), with this variation being representative of the target displacement and being measured on the fixed electromagnet (507). The inductance measurement can be performed by modulating an AC signal onto the magnetisation current of one coil and measuring the amplitude variation of this AC coupled signal on the other. The AC signal frequency would typically be at least an order of magnitude higher than paddle displacement frequency for sufficient sensing resolution.

In an alternative arrangement, in order to maximise the coupling between the two inductor circuits, a measurement electromagnet (3) can be placed at the channel input, and the mutual inductance variation caused by the displacement of the moving element (504) can be measured between the electromagnet (3) at the channel input and the electromagnet (1) on the moving element (504), while the electromagnet (507) downstream in the flow channel will only provide the magnetic repulsive force. It is advantageous that the gap between the electromagnet (1) on the moving element (504) and the measurement electromagnet (3) is minimised in order to increase the response. It is understood that in this alternative arrangement the fixed electromagnet (507) could be replaced by a permanent magnet.

In the arrangements described above, the variation of the inductance on the electromagnets is measured by the electronics connected to the measurement electromagnet through a flex cable (710), and is sent to a processing unit where it will be translated into a flow measurement.

Figure 6A:
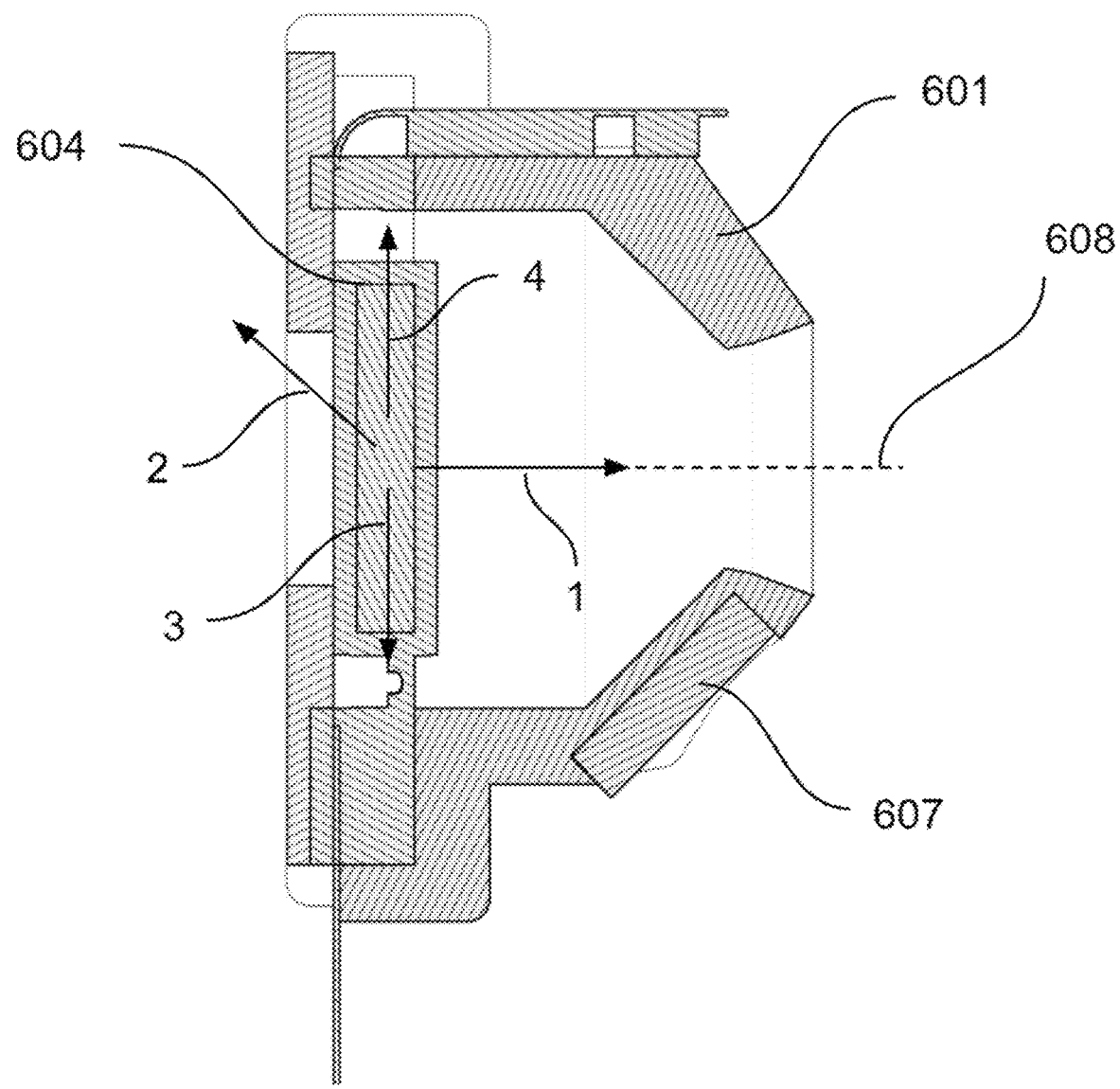
FIG. 6A, which depicts the forces acting on the moving member in the expected operating condition of the flow sensor, when the flow channel central axis is parallel to the horizontal.
Figure 6B:
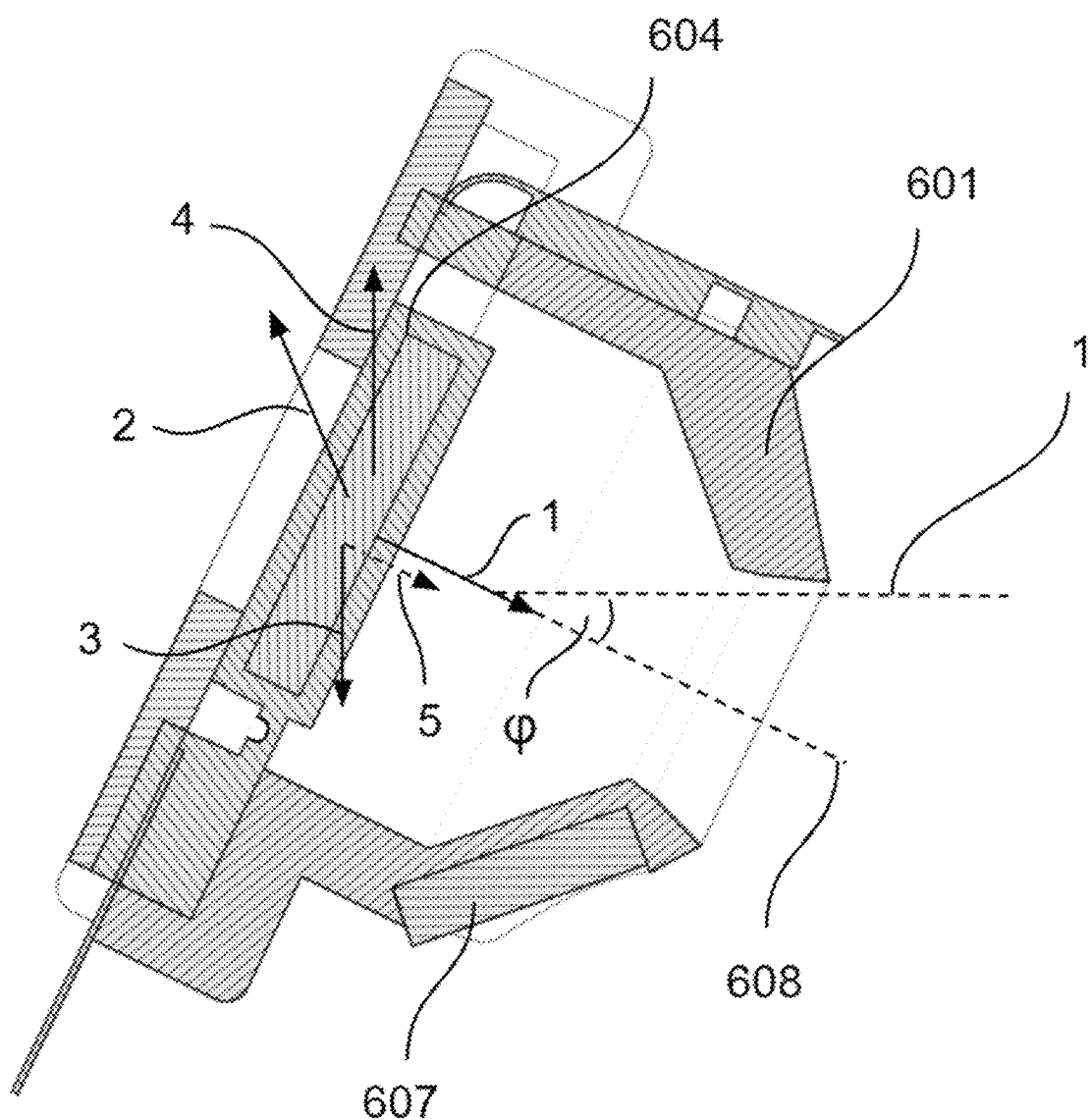
FIG. 6B depicts the forces acting on the moving member when the flow channel central axis is at an angle 'o' with respect to the horizontal.

Referring to FIG. 6A and FIG. 6B, in the normal sensor operation the hinged target (604) is subjected to different forces, the main being the drag force (1) from the fluid medium resultant from a flow of fluid through the fluid channel, and the magnetic repulsive force (2) from the fixed magnet (607) downstream in the channel. Additional forces to which the hinged target (604) is subjected during the sensor operation are gravity (3) and the buoyancy reaction of the fluid (4), which depends on the target volume and on the density of the fluid medium.

FIG. 6A depicts the general operating condition, where the rigid housing (601) of the flow sensing unit lays horizontally, with the fluid flow perpendicular to the direction of the gravity (3) acting on the target (604). In this arrangement, the component of the gravity force parallel to the direction of the flow (608) is zero, and the target deflection, and so the channel opening, only depends on the balance between the drag force (1) and the magnetic repelling force (2).

FIG. 6B depicts an alternative operating condition where the flow channel housing (601) is at an angle 'φ' with respect to the horizontal. In this case, the component (5) of the gravity force (3) parallel to the direction of the flow (608) is not null anymore and its effect on the hinged target (604) will add to the total balance of forces (1, 2) resulting in a measurement error of the target displacement, and so of the fluid flow, especially for very low flow rates where the effect of gravity could be comparable to the drag force. In order to improve the accuracy and reliability of the sensing unit at any orientation, it will be advantageous to implement a buoyancy compensation on the hinged target in the flow channel, so as to remove or reduce the gravity effect. The buoyancy compensation can be implemented by design, by manufacturing the moving target with appropriate materials/geometry so that the equivalent density of the target assembly matches the density of the fluid under investigation. Alternatively, or in addition to that, a numerical compensation can be introduced, and the output from a sensor such as an accelerometer, gyroscope or position sensor can be calibrated to continuously detect the orientation of the sensing unit and to digitally remove the gravity effect during the measurements.

Figure 7A:
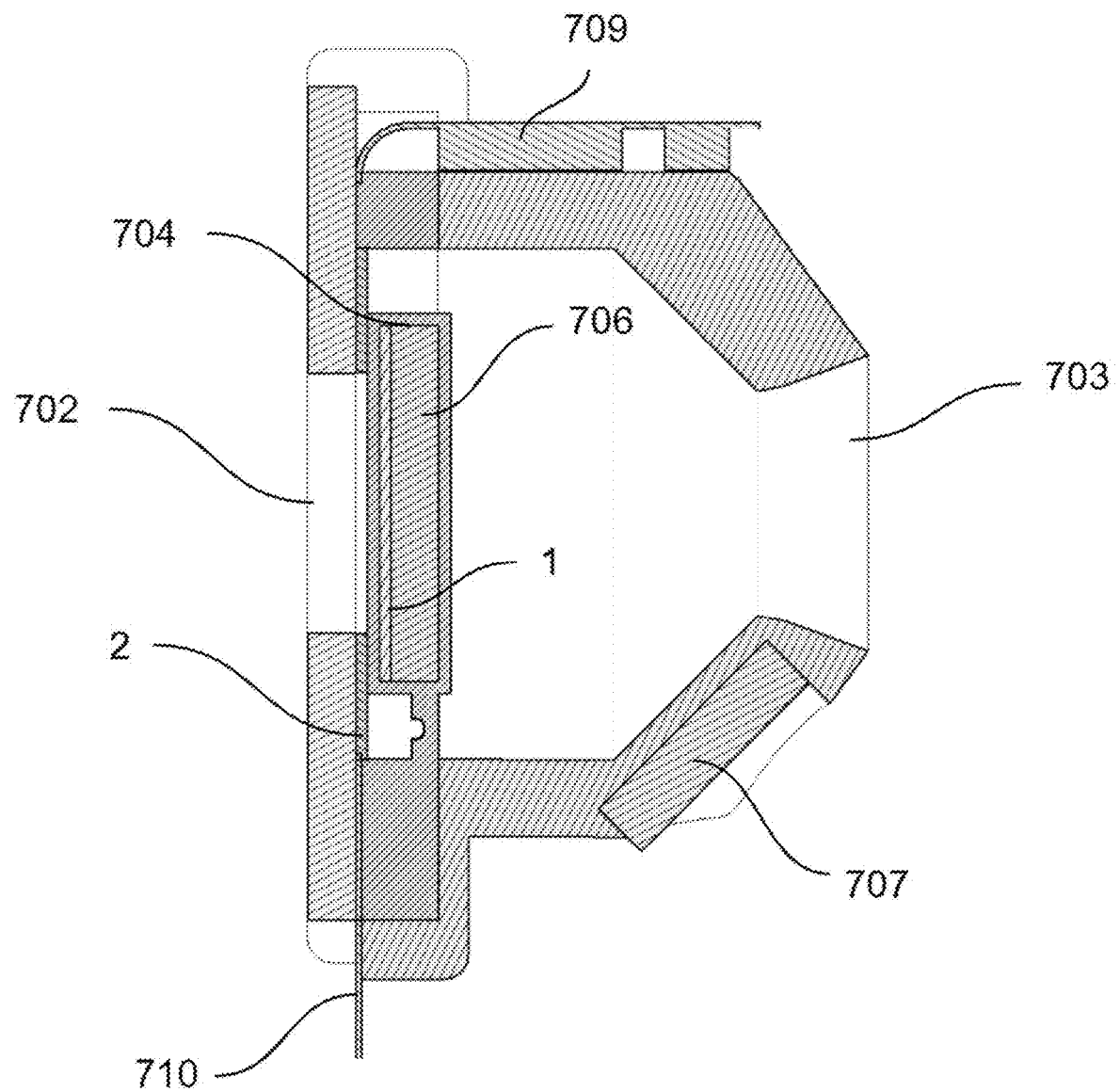
FIG. 7A is a schematic representation of the lateral section of the flow channel in an alternative arrangement of the device of the present teaching, where the displacement of the moving member is measured via capacitive sensing technology by means of a pair of capacitive plates, one on the moving member and one fixed and close to the channel input, transverse to the fluid direction, with the fluid medium as the dielectric.

FIG. 7A presents the lateral section of the flow channel in one alternative arrangement of the sensing unit of the present teaching, where the displacement of the moving target (704) is measured via capacitive sensing technology. In this arrangement the moving element (704) is formed by a permanent magnet (706) and by an element constituting one plate (1) of a variable capacitor, while the other plate (2) is located on the fluid channel, close to the channel input (702) and transverse to the direction of the flow. In conditions of non-zero flow, the displacement of the target (704) will cause a variation in the distance between the two capacitor plates (1, 2) and so of the capacitance reading, with the fluid medium as a dielectric. The capacitance is measured by the sensing electronics (709) connected to the capacitor plates (1, 2) through a flex cable (710), and is sent to a processing unit where it will be translated into a flow measurement. As an exemplary arrangement, the fixed capacitor plate (2) can be ring-shaped to be easily mounted onto the channel walls, or it can have a circular section and be suspended into the channel, as long as the capacitor plates have as large a common area as possible to maximise capacitance.

Figure 7B:
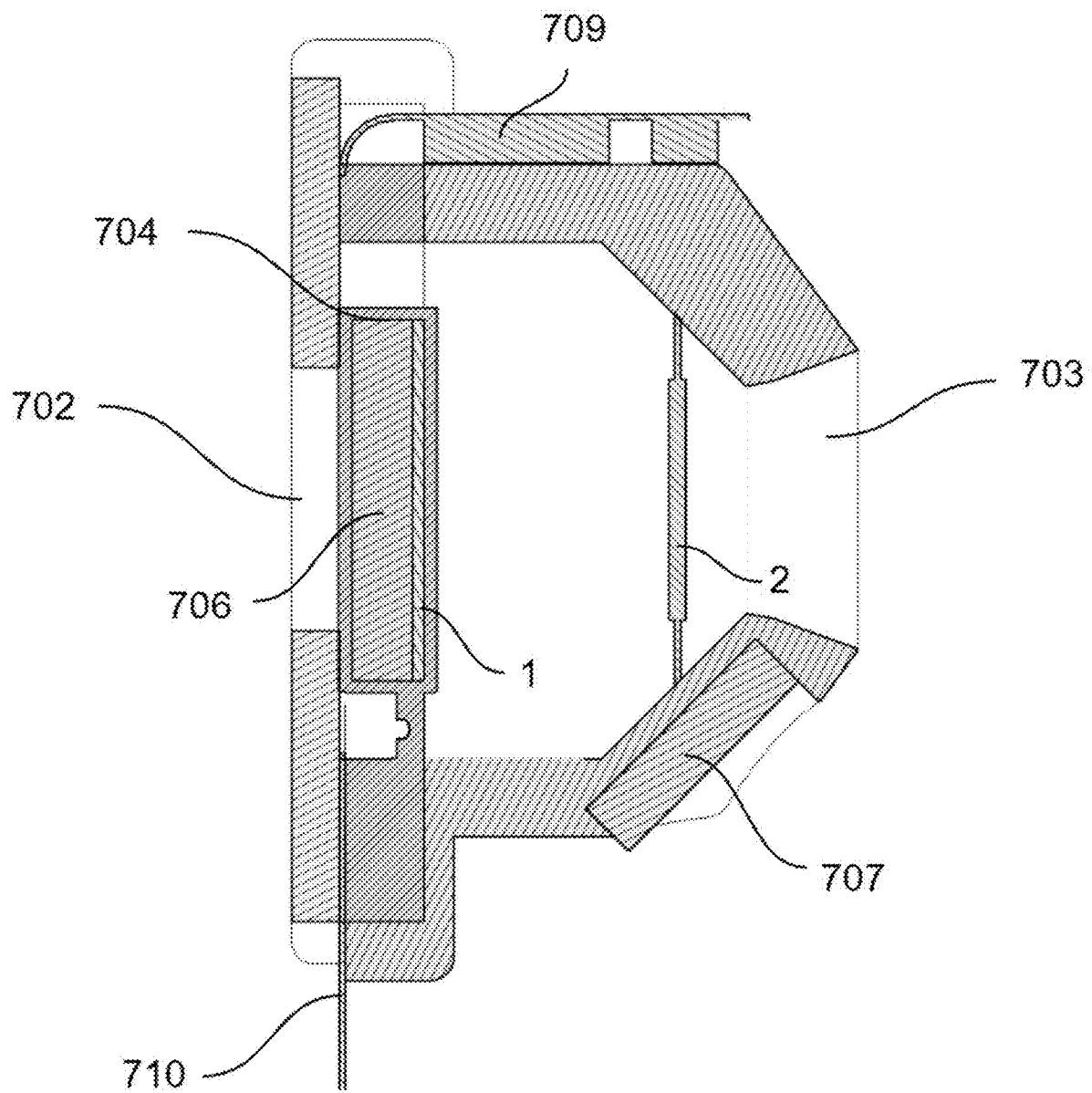
FIG. 7B is a schematic representation of the lateral section of the flow channel in an alternative arrangement of the device of the present teaching, where the displacement of the moving member is measured via capacitive sensing technology by means of a pair of capacitive plates, one on the moving member and one fixed and close to the channel output, transverse to the fluid direction, with the fluid medium as the dielectric.

FIG. 7B presents the lateral section of the flow channel in one alternative arrangement with respect to the one presented in FIG. 7A, where the fixed plate (2) of the variable capacitor is a plate with a circular cross-section and is placed close to the channel output (703), and transverse to the direction of the flow.

It is important that the capacitor plate (1) on the moving element (704) is always facing the fixed plate (2) in the flow channel, so it will be placed on the left side of the permanent magnet (706) on the moving target (704) in the exemplary arrangement of FIG. 7A, and on the right side of the permanent magnet (706) on the moving target (704) in the exemplary arrangement of FIG. 7B. The capacitor plates of FIG. 7A-B can be advantageously covered with an insulating layer to avoid contact with the fluid and prevent fouling and corrosion, which could introduce errors in the capacitance readings. In either arrangement, the addition of static capacitor plates on the channel wall could aid in resolving the baseline permittivity of the fluid dielectric, thereby serving as a reference value for the variable capacitance.

Figure 8A:
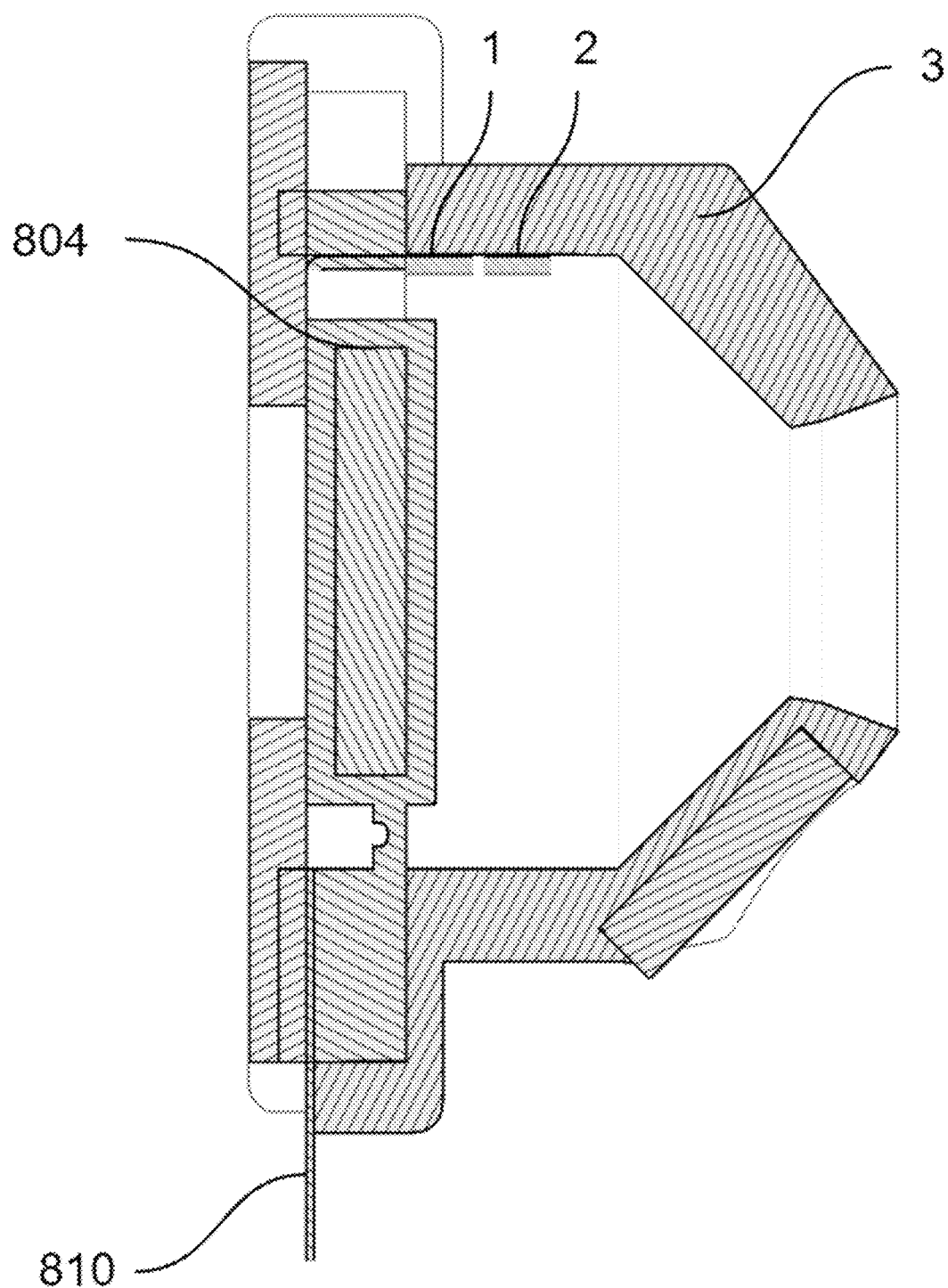
FIG. 8A is a schematic representation of the lateral section of the flow channel in an alternative arrangement of the device of the present teaching, where the displacement of the moving member is measured via optical sensing technology by means of one or more optical transducers placed on the channel wall and inside the flow channel.
Figure 8B:
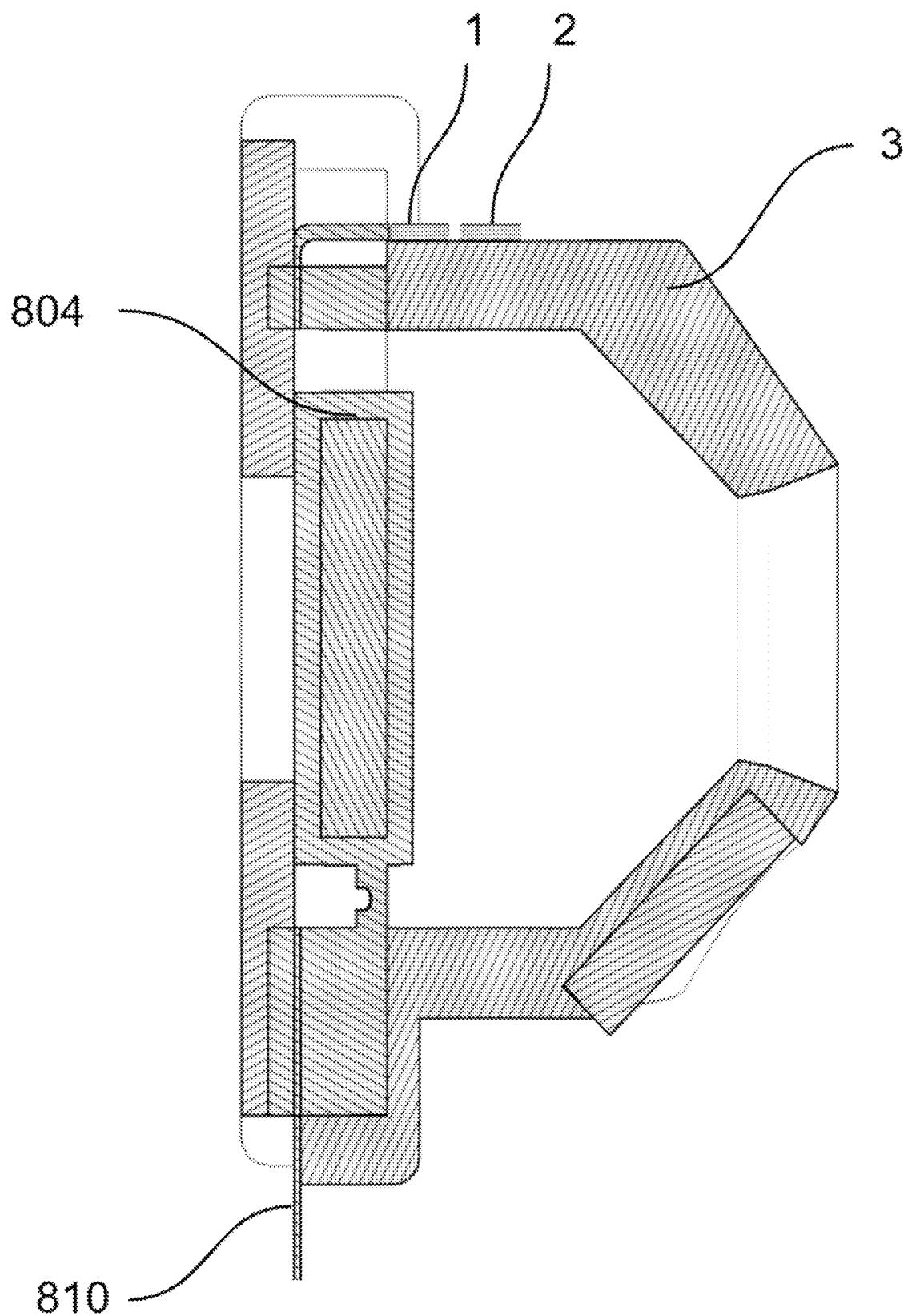
FIG. 8B is a schematic representation of the lateral section of the flow channel in an alternative arrangement of the device of the present teaching, where the displacement of the moving member is measured via optical sensing technology by means of one or more optical transducers placed on the channel wall and outside the flow channel.

FIG. 8A and FIG. 8B present the lateral section of the flow channel in alternative arrangements of the sensing unit of the present teaching, where the displacement of the hinged target (804) is detected via optical sensing technology.

In the exemplary arrangement of FIG. 8A, one or more optical transducers (1, 2) are located on the channel wall (3) inside the flow channel, parallel to the direction of the flow and in contact with the fluid. Depending on the optical sensing method selected for each application, an emitting member (1) sends a series of light pulses towards the moving member (804) which reflects them back to a receiving member (2). In conditions of non-zero flow, the displacement of the moving member (804) can be detected via optical time-of-flight, Doppler shift or interferometric methods depending on the characteristics of the light reflected by the moving member (804). The signal from the optical transducers (1, 2) is measured by the electronics connected to the sensing unit through a flex cable (810) and is sent to a processing unit where it will be translated into a flow measurement.

FIG. 8B presents an alternative arrangement of the one depicted in FIG. 8A, where one or more optical transducers (1, 2) are located externally on the channel wall (3) and parallel to the direction of the flow. In this arrangement, the flow channel should be manufactured with an optically transparent material in order to allow for the light transmission between the optical transducer (1, 2) and the moving member (804) through the channel wall (3).

Figure 9A:
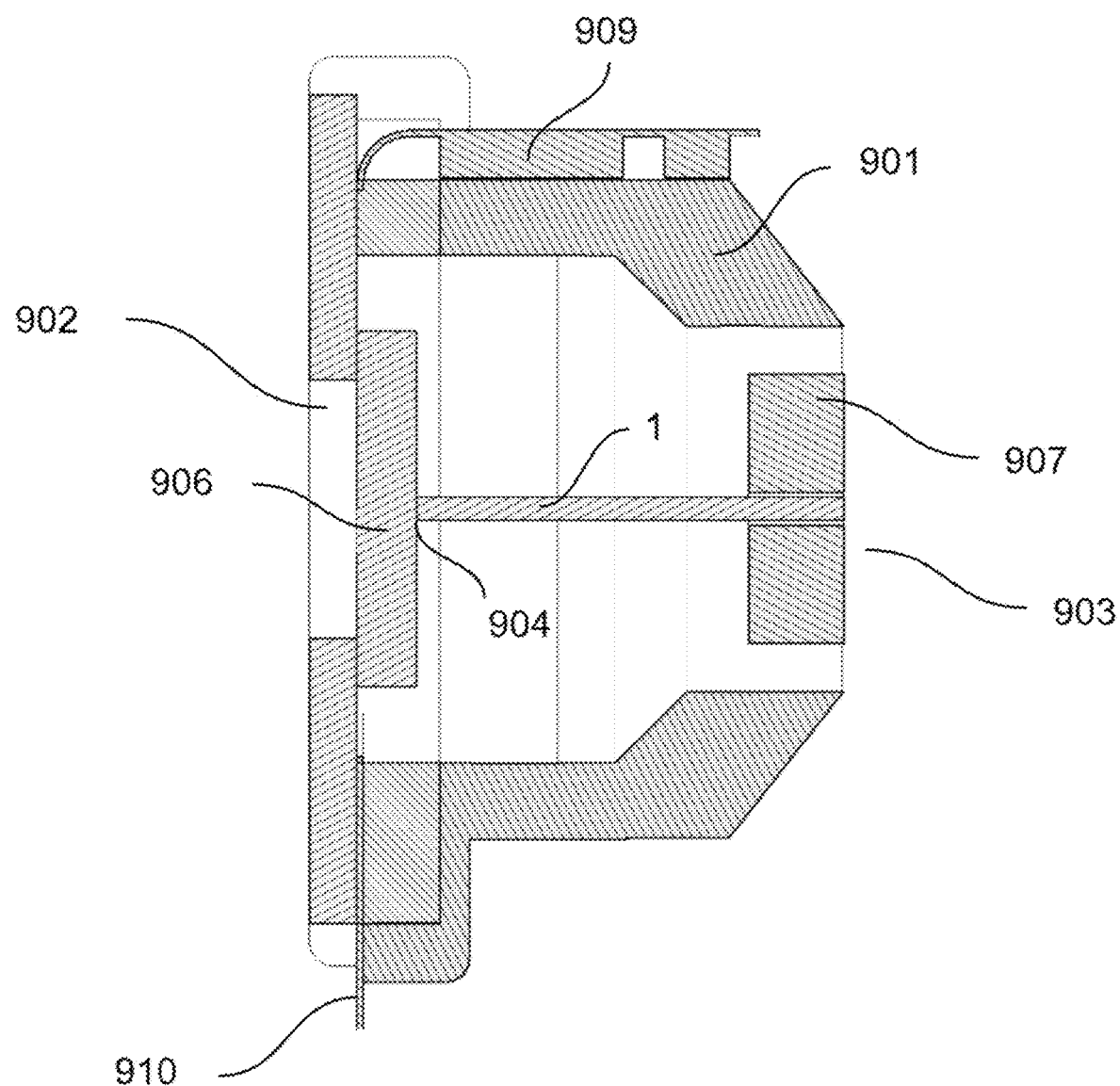
FIG. 9A and FIG. 9B are a schematic representation respectively of the lateral and front section of the flow channel in an alternative arrangement of the device of the present teaching, in conditions of zero flow, where the moving member in the flow channel is a permanent magnet whose displacement is parallel to the flow direction, and where the fixed magnet is placed downstream, in the middle of the flow channel and parallel to the moving member.
Figure 9B:
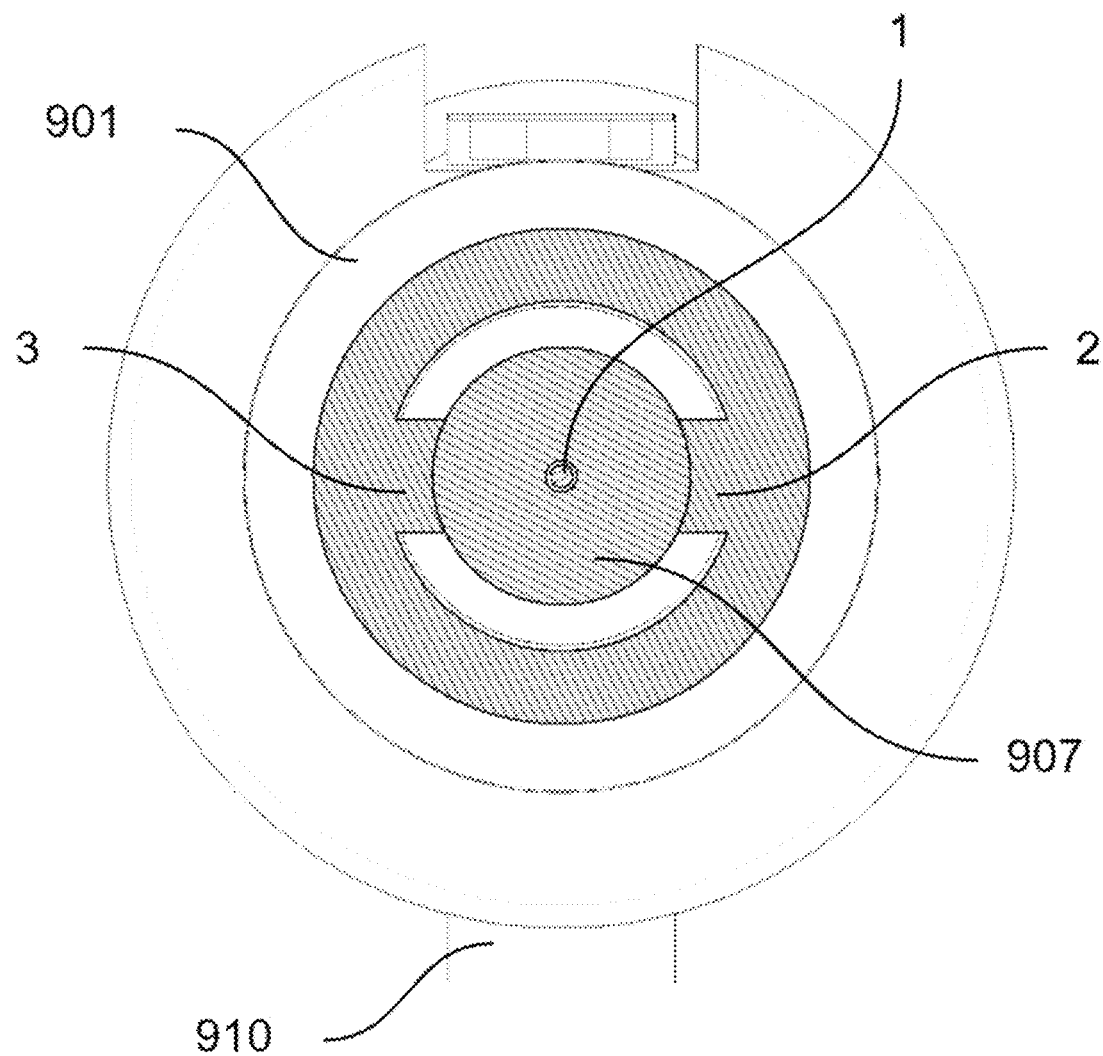

FIG. 9A and FIG. 9B present another low-friction arrangement of the present teaching, in conditions of zero flow, where a moving member (904) is mounted in a rigid housing (901) forming a flow channel, transverse to the direction of the fluid flow and close to the channel input port (902), said moving member (904) being a target formed from a permanent magnet (906) and a supporting member (1) parallel to the direction of the flow, on which moving member the fluid will exert a drag force. A fixed member (907), which is a permanent magnet, is placed between the input port (902) and the output port (903) of the flow channel, closer to the output port (903) and transverse to the fluid flow. The two permanent magnets (906, 907) have their faces of like polarity facing each other, so that the fixed member (907) exerts a counteracting magnetic force on the moving member (904) and limits its displacement proportionally to the magnitude of the drag force. The fixed member (907) can advantageously be ring shaped in order to offer a sliding constraint to the supporting member (1) of the target (906), minimising the friction of the sliding movement.

As shown in the exemplary arrangement of FIG. 9B, the fixed member (907) can be suspended in the channel through one or more supporting structures (2, 3) so to not occlude the channel output. In this exemplary arrangement, the displacement of the moving member in the channel is parallel to the fluid flow and the permanent magnet (906) on the target no longer requires a living hinge. A sensing means (909) can be located on the outside of the flow channel, perpendicular to the moving member (904) and in its proximity, said sensing means measuring the displacement of the moving member (904). The signals received by the sensing means (909) are sent to a processing unit via a flex cable (910) and are translated into a flow measurement.

Figure 10A:
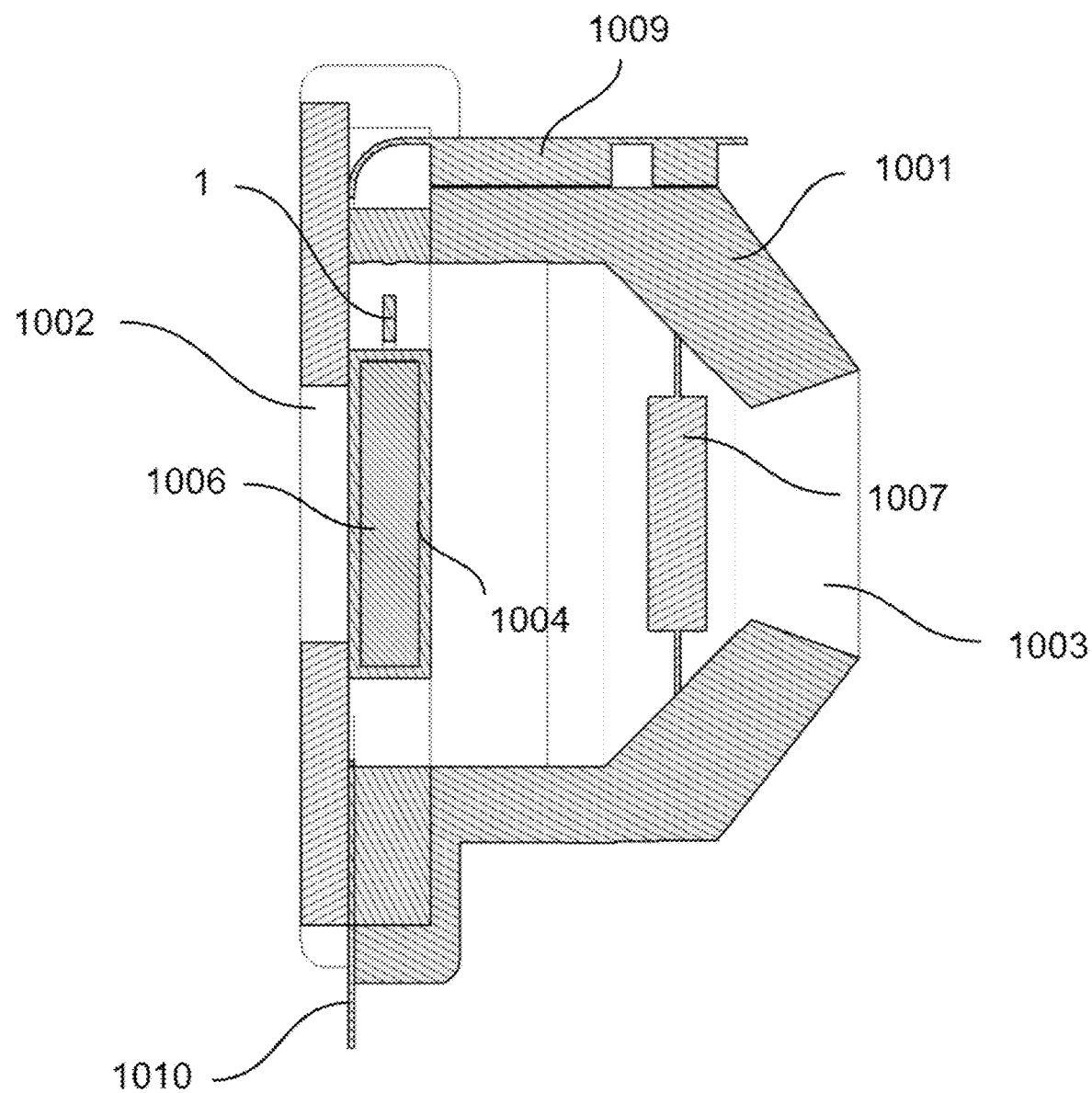
FIG. 10A and FIG. 10B are a schematic representation respectively of the lateral and front section of an alternative arrangement of the device of the present teaching, in conditions of zero flow, where the moving member in the flow channel is supported by a plurality of living hinges such that the motion of said member remains perpendicular to the flow.
Figure 10B:
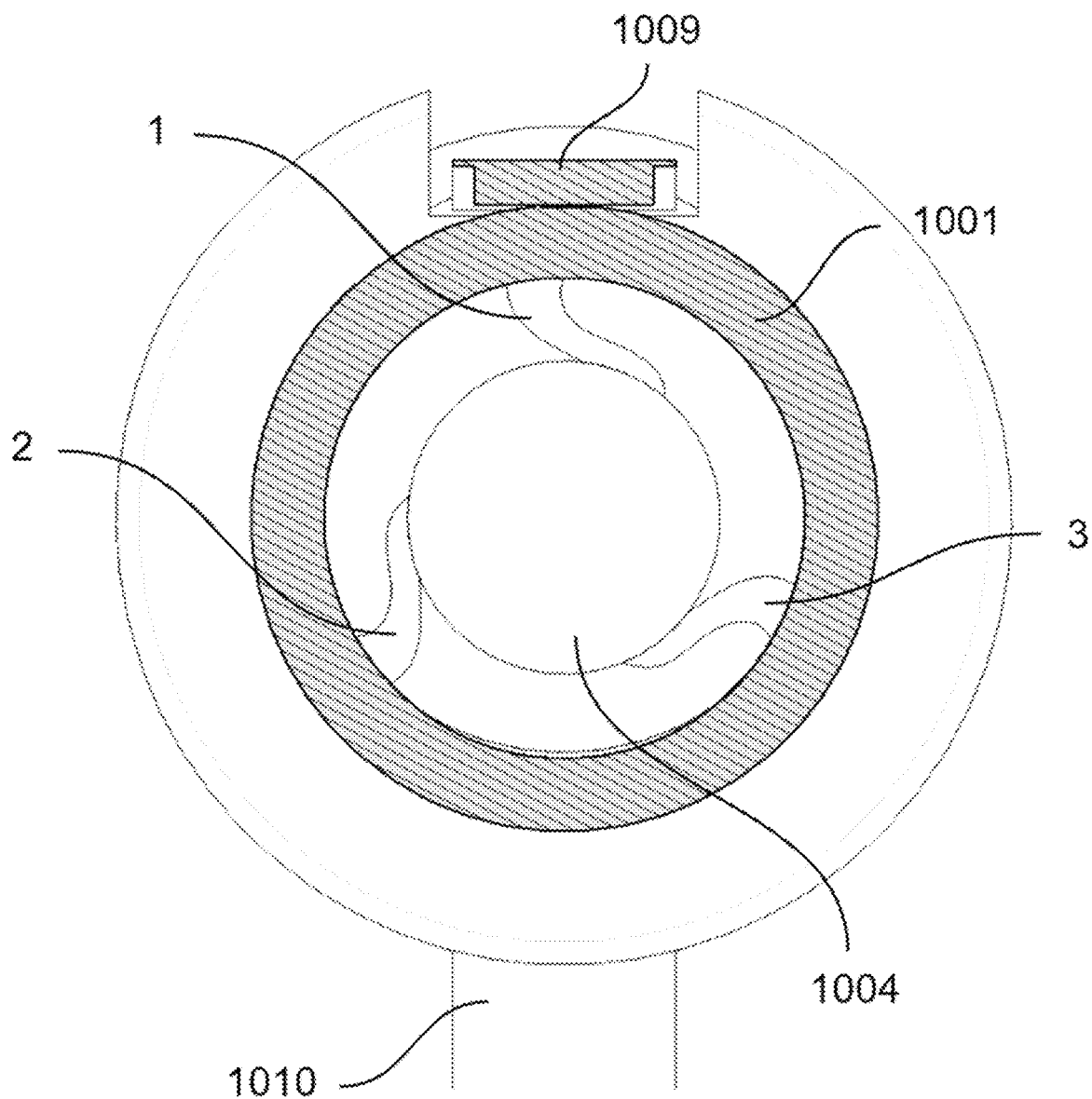

FIG. 10A presents an alternative arrangement of the present teaching, in conditions of zero flow, where a moving member (1004) is mounted in a rigid housing (1001) forming a flow channel, transverse to the direction of the fluid flow and close to the channel input port (1002), said moving member (1004) being a target formed from a permanent magnet (1006) and supported by a plurality of living hinges (1, 2, 3) such that the motion of the moving member (1004) remains transverse to the flow. As shown in FIG. 10B, the living hinges (1, 2, 3) allow suspending the moving member (1004) in the middle of the flow channel, with the geometry and material for the living hinges (1, 2, 3) to be defined according to the selected application.

A fixed member (1007) formed from a permanent magnet is placed between the input port (1002) and the output port (1003) of the flow channel, closer to the output port (1003) and transverse to the fluid flow, with the faces of like polarity on the two permanent magnets (1006, 1007) facing each other to generate a magnetic repulsive force. As shown in this exemplary arrangement, the fixed member (1007) can have a circular cross-section and be suspended in the channel by gluing or other clamping means, however, it can also be ring shaped and clamped to the channel walls in order to not restrict the cross sectional area of the flow channel, as shown in the exemplary arrangement of FIG. 9A-B. The fixed member (1007) will exert a counteracting magnetic force on the magnet (1006) on the moving member (1004) and will limit its displacement proportionally to the flow rate. In this exemplary arrangement a sensing means (1009) can be located on the outside of the flow channel, perpendicular to the moving member (1004) and in its proximity, said sensing means measuring the displacement of the moving member (1004). The signals received by the sensing means (1009) are sent to a processing unit via a flex cable (1010) and are translated into a flow measurement.

Figure 11:
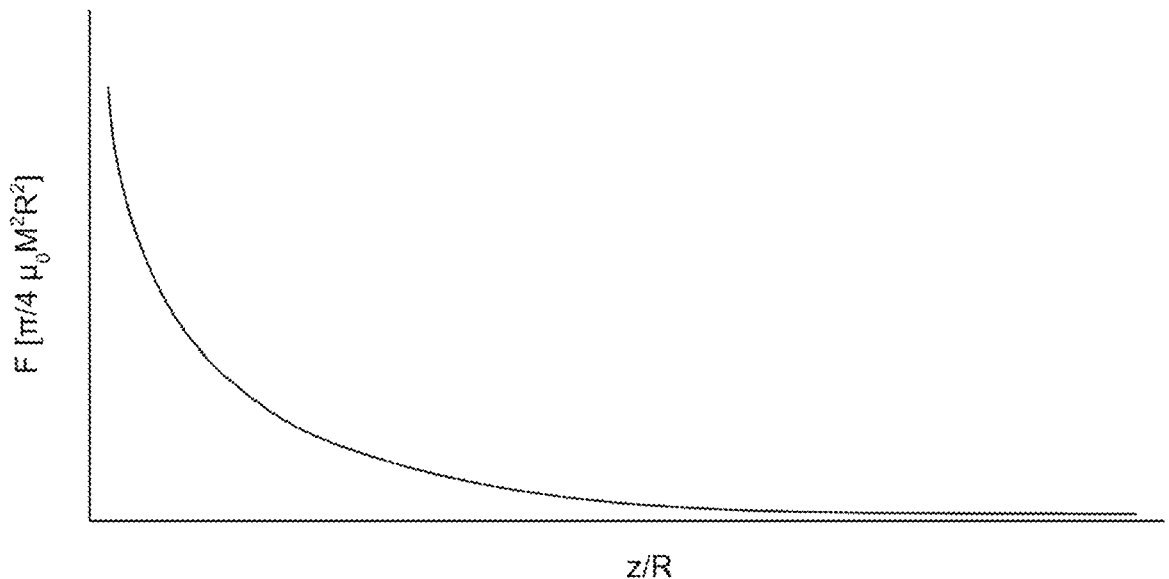
FIG. 11 is a representation of the relationship between the magnetic force on two cylindrical magnets with radius r equal to their length L, and their separation distance.

FIG. 11 depicts the relationship between the magnetic force between two cylindrical shaped magnets of radius R and length L, where R=L, and the ratio of their separation distance z and their radius R, where the force is an attractive force if the two magnets' poles with opposite polarity are facing, and a repulsive force when the magnets' poles with same polarity are facing. From the trend line in the graph it is clear how the magnetic force between the two magnets becomes very high as the two magnets approach each other, and instead rapidly decreases when they are separated, following ideally a $4^{th}$ order polynomial law when the magnets are aligned along the axis of their magnetic dipoles.

Figure 12:
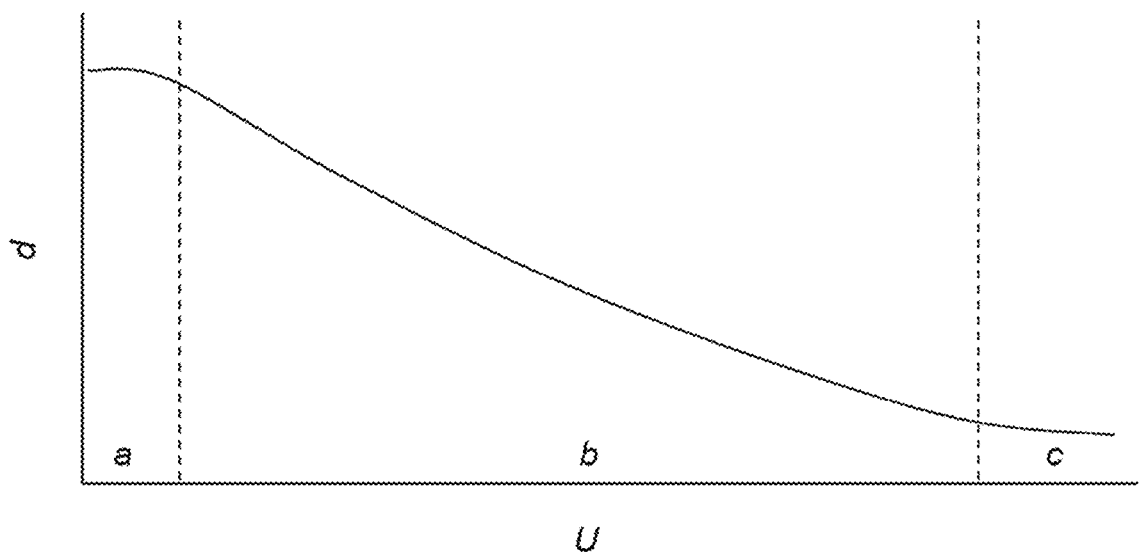
FIG. 12 is a representation of the calibration function for the flow sensor of the present teaching, showing the relationship between the sensor output and the flow rate.

FIG. 12 describes the calibration function for the flow sensor of the present teaching, and in particular it shows the relationship between the magnetic field reading from the sensing unit (d), proportional to the target displacement, and the flow rate (U) of the fluid in the channel.

In conditions of zero flow (U=0), the distance between the magnet on the target and the fixed magnet in the flow channel is maximum, the target is in its resting position against the channel input and the sensor output corresponds to the saturation point (a). When the pressure differential between the channel input and output exceeds the magnetic repulsion force between the two magnets, the target is moved away from the channel input and the channel opens. As flow increases, the target moves further away from the channel input, with the magnetic repulsive force counteracting the drag force of the fluid on the target, and so limiting its displacement. This results in the linearisation of the relationship between the sensor output (d), representative of the target displacement, and the flow rate (U) as shown in the (b) region of the graph.

Once the target reaches its maximum displacement position, the magnetic repulsive force is maximised and the magnetic field reading from the sensing unit reaches the opposite saturation point (c). The sensor dynamic range will then correspond to the linearised curve in region (b), which can be extended depending on the parameters of the selected magnets and their separation distance in the flow channel.

Figure 13A:
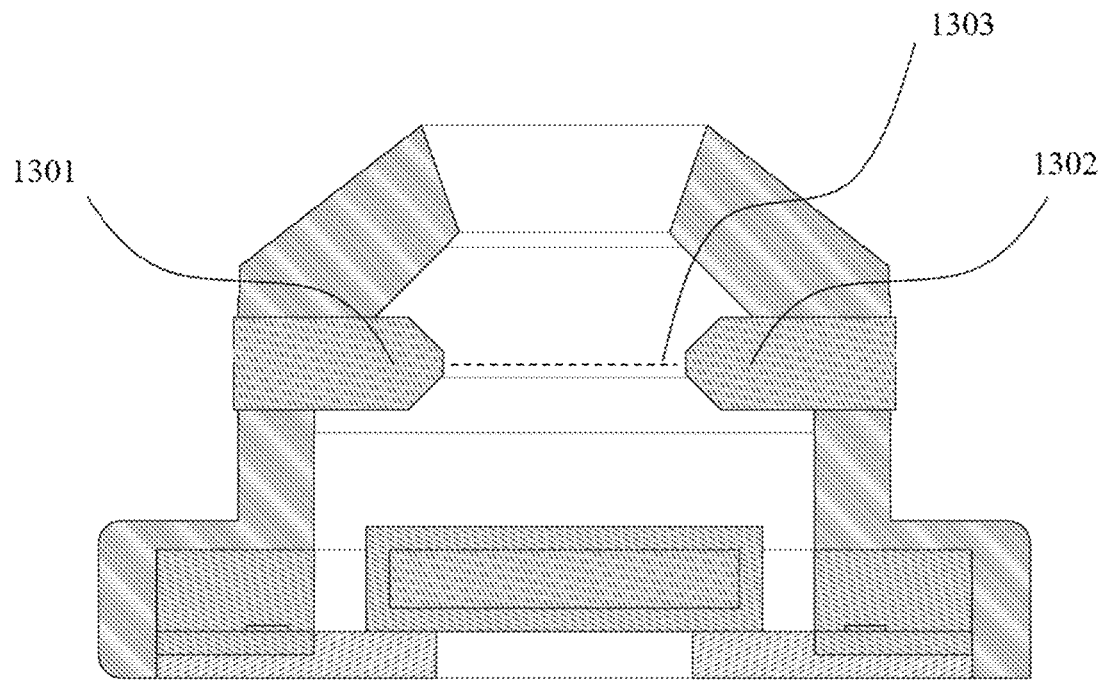
FIG. 13A is a schematic representation of the lateral section of the device containing embedded conductivity sensing pins, which can be used along with a signal to differentiate between different media passing through the channel via the application of a signal.

FIG. 13A presents an alternative arrangement of the present teaching, with the addition of conductivity sensing technology to differentiate between different bulk media passing through the channel. Two electrically conductive fixed members (1301 and 1302), embedded in the flow channel wall, act as conductivity electrodes. When an AC signal is applied across the electrodes, the resulting impedance along the conductive path (1303) is used to determine whether the bulk material in the channel is a liquid or gas. The conductivity sensor readings are used to differentiate between gas and conductive liquids e.g. (tap water, milk, blood, urine) in the channel in order to prevent phantom readings for liquid flow. where the electrodes are pins made from an electrically conductive metal such as brass, or a material with an electrically conductive coating such as gold.

The electrodes may be made from or coated with a material that neither corrodes or degrades in the presence of liquid, such as platinum, gold or 316 stainless steel.

Desirably the electrode pins contain a pointed tip to prevent skinning of liquids with higher surface tension. An alternating current (AC) signal can used to prevent electrode polarisation and ion deposition. If used, such an alternating current signal can be applied between the electrodes to derive an impedance measurement distinguishing bulk liquid from surface wetting.

The conductivity sensor can be coupled to the connecting cable to effect communication of the stimulus and output signals to peripheral devices, the device further comprising an analog-to-digital converter (ADC) to read the output signal as well as drive electronics to generate the AC stimulus.

The conductivity pins may be configured to serve a secondary purpose of acting as a hard-stop for paddle motion. This can prevent the paddle opening too far and thus locking in undesirable positions. It also limits paddle flexion and thereby paddle fatigue.

Figure 13B:
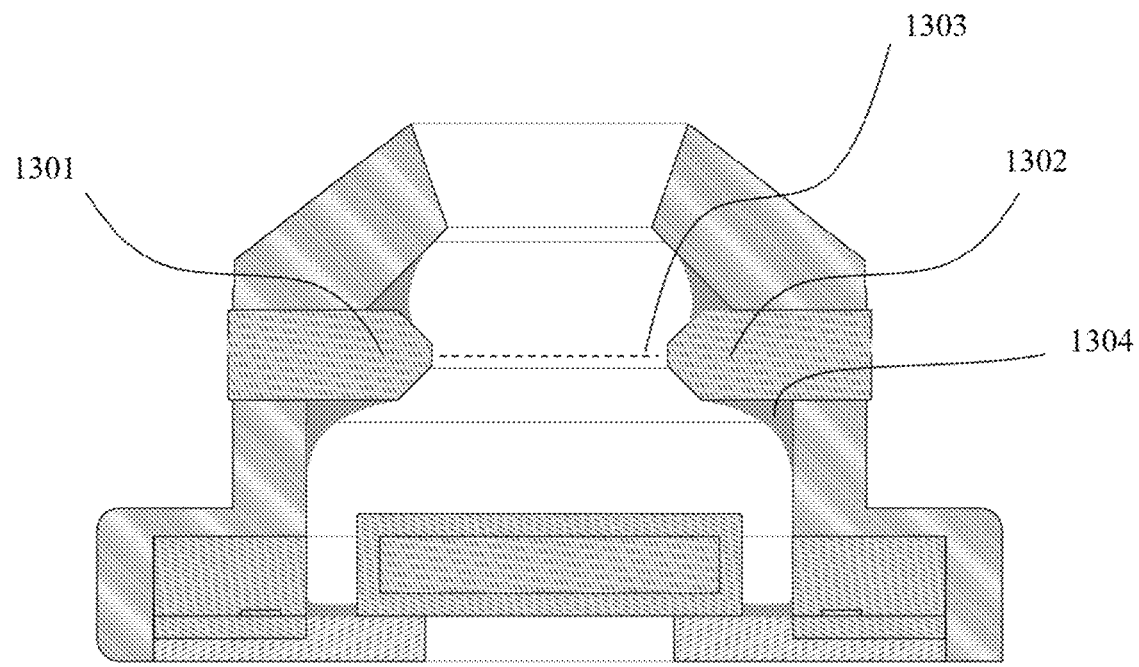
FIG. 13B is a schematic representation of the lateral section of the device containing embedded conductivity sensing pins, where the bulk material in the channel is air but their consists a liquid skin on the surface of components inside the channel.

FIG. 13B depicts an alternative operating condition where the bulk material in the channel is air (or some other gas) but with a skin of liquid (1304) present on surfaces inside the channel. Molecules within a fluid are attracted to and bind with surrounding molecules. However, those on the surface are only bonded to molecules beneath them. Consequently, the top layer experiences a net force, compressing the surface molecules and creating a 'skin' on the fluid's surface. This surface tension enables the fluid to resist certain external forces such as gravity. This is the case in FIG. 13B, where fluid remains on the internal surface of the channel due to the skinning effect, even though the bulk media in the channel is air. This could lead to false readings, where water is incorrectly categorised as the bulk media in the channel.

Figure 13C:
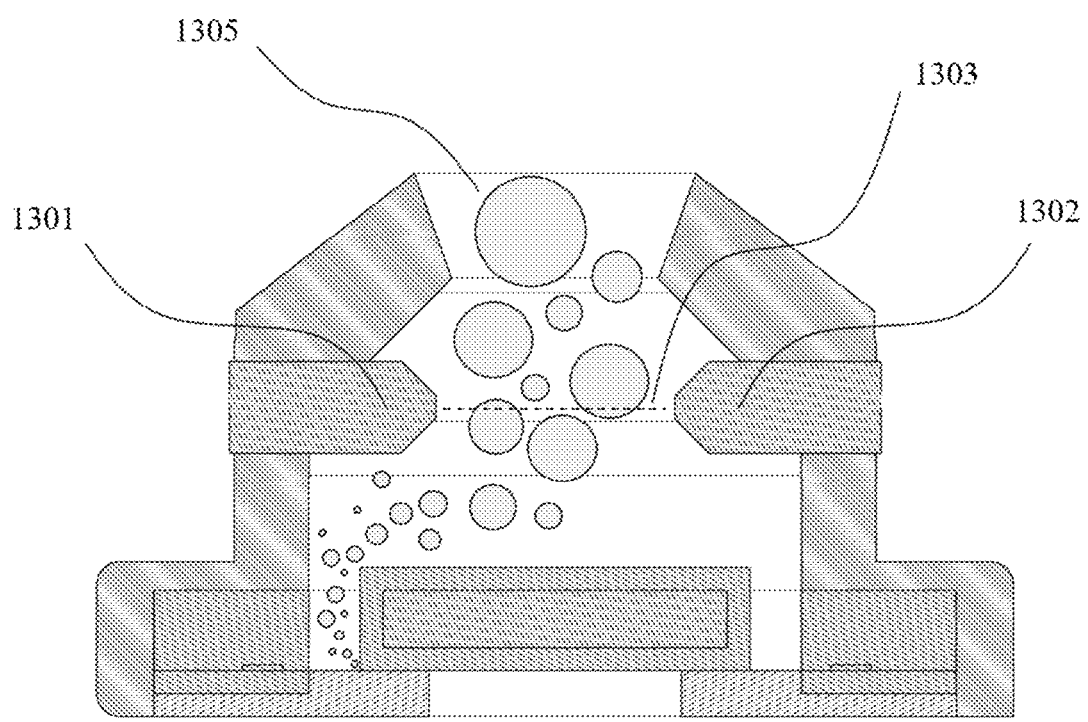
FIG. 13C is a schematic representation of the lateral section of the device containing embedded conductivity sensing pins, where the bulk material is a liquid, however there is bubble formation due to air or another gas being present in the bulk liquid.

FIG. 13C depicts an alternative operating condition where both liquid and gaseous media (in the form of bubbles) (1305) pass through the channel. In this case, the conductivity pins will detect the presence of air due to decreased and/or fluctuating conductivity readings.

The invention claimed is:

1. A flow measurement device comprising:
   a. A rigid housing defining a flow channel having a channel input and a channel output, the flow channel being configured to allow a fluid medium to flow from the channel input to the channel output;
   b. A moving member mounted within the flow channel, and extending transverse to a direction of flow of the fluid medium, the moving member comprising a moving member magnet, the moving member magnet operatively moving on exposure to a drag force resultant from fluid passing in the flow channel;
   c. A fixed magnet, provided at least proximal to a sidewall of the flow channel, the fixed magnet having like polarity with respect to moving member magnet, and being arranged to operatively exert a consistent repulsive force on the moving member magnet thereby limiting its displacement proportionally to the magnitude of the drag force exerted by the fluid flow, so to linearise a relationship between a rate of flow of the fluid medium and moving member magnet displacement;
   d. A sensing element located relative to the moving member magnet and configured to provide an output indicative movement of the moving member magnet within the flow channel; and
   wherein the moving member magnet comprises a permanent magnet located transverse to the fluid flow, whose displacement is parallel to the direction of flow of the fluid medium and which is connected to a support parallel to the direction of flow of the fluid medium, and where the fixed magnet is placed downstream, in a middle of the flow channel and transverse to the fluid flow.

2. The flow measurement device of claim 1, where the moving member is connected to a sliding pin coupled to the flow channel through a sliding constraint, and so that friction during the sliding movement is minimised.

3. The flow measurement device of claim 1, where the fixed magnet is ring shaped in order to not obstruct the channel cross section and to provide support for the moving member.

4. The flow measurement device of claim 1, where the position of the moving member is detected via sensing technology.

5. The flow measurement device of claim 1 wherein the sensing element is coupled to a connecting cable to effect communication of the output signal to peripheral devices, the device further comprising an amplifier configured to amplify the output signal in the vicinity of the flow channel and before transmission through the connecting cable in order to avoid external interference which may be coupled within the cable.

6. The flow measurement device of claim 1 configured to provide active amplification of the output signal, the active amplification being provided by at least one amplifier configured to provide amplification of the output signal to a level such that a zero flow signal reading is proximate to a maximum value of a subsequent analog-to-digital converter, ADC, in order to maximise signal resolution.

7. The flow measurement device of claim 1 comprising a processing unit in communication with the sensing element, the processing unit being configured to receive output signal and converting it to a flow measurement value using a calibration function, said function employing a parameterised model, look-up-table, LUT, interpolated values, or any combination thereof.

8. The flow measurement device of claim 1 comprising a memory element for storing calibration coefficients of the sensing element, or for storing sensor wear and/or use information.

9. The flow measurement device of claim 1, wherein the device is a biomedical device and configured to detect real-time linear or pulsatile flow in a biomedical application.

10. The flow measurement device of claim 1 configured to measure the a flow of fluids, wherein the fluid is in the form of a gas or a liquid.

11. The device of claim 1, wherein the flow channel contains a conductivity sensor consisting of two or more electrodes in the flow channel.

12. The flow measurement device in claim 11, wherein the conductivity sensor readings are used to differentiate between gas and conductive liquids in the flow channel in order to prevent phantom readings for liquid flow.

13. The flow measurement device in claim 11, wherein the electrodes are pins made from an electrically conductive metal.

14. The flow measurement device in claim 13, wherein the electrodes are made from or coated with a material that neither corrodes or degrades in the presence of liquid, such as platinum, gold or 316 stainless steel.

15. The flow measurement device in claim 13, wherein the electrode pins contain a pointed tip to prevent skinning of liquids with higher surface tension.

16. The flow measurement device in claim 11, wherein an alternating current signal is used to prevent electrode polarisation and ion deposition.

17. The flow measurement device in claim 11, wherein an alternating current signal is applied between the electrodes to derive an impedance measurement distinguishing bulk liquid from surface wetting.

18. A measurement system comprising:
   the flow measurement device as claimed in claim 1;
   a processing unit; and,
   a visual display, wherein the processing unit is configured to receive sensing element data from the flow measurement device and provide, in the visual display, a visual indication of a measured flow.

19. The measurement system of claim 18, wherein the processing unit is a smartphone, the visual display being a screen of the smartphone, the smartphone having executing thereon application software that receives and processes flow sensor data from a sensor and provides, in the visual display, a visual indication of the flow measured.

* * * * *